US011107852B2

(12) United States Patent
Kosuda et al.

(10) Patent No.: US 11,107,852 B2
(45) Date of Patent: Aug. 31, 2021

(54) LIGHT RECEIVING ELEMENT HAVING LIGHT BLOCKING SECTION COVERING AT LEAST PART OF AMPLIFIER CIRCUIT, LIGHT RECEIVING MODULE, PHOTOELECTRIC SENSOR AND BIOLOGICAL INFORMATION MEASUREMENT

(71) Applicant: SEIKO EPSON CORPORATION, Tokyo (JP)

(72) Inventors: Tsukasa Kosuda, Matsumoto (JP); Atsushi Matsuo, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 257 days.

(21) Appl. No.: 16/365,822

(22) Filed: Mar. 27, 2019

(65) Prior Publication Data

US 2019/0305032 A1    Oct. 3, 2019

(30) Foreign Application Priority Data

Mar. 28, 2018    (JP) .............................. JP2018-061293

(51) Int. Cl.
| *A61B 5/024* | (2006.01) |
| *H01L 27/146* | (2006.01) |
| *A61B 5/00* | (2006.01) |
| *A61B 5/1455* | (2006.01) |

(52) U.S. Cl.
CPC .... *H01L 27/14645* (2013.01); *A61B 5/02427* (2013.01); *A61B 5/14551* (2013.01); *A61B 5/7203* (2013.01)

(58) Field of Classification Search
CPC ......... H01L 27/14603; H01L 27/14609; H01L 27/14623; H01L 27/14636; H01L 27/14645; H01L 27/144; H01L 27/146; H01L 29/00; H01L 31/02164; H01L 31/167; A61B 5/02427; A61B 5/7203; A61B 2562/0233; A61B 5/14552; A61B 5/02108; A61B 5/02416; A61B 5/02438; H04N 5/353; H03F 3/04
USPC ................................ 250/214 R, 214.1, 208.1
See application file for complete search history.

(56) References Cited

U.S. PATENT DOCUMENTS

| 7,196,311 B2 | 3/2007 | Takiba et al. |
| 7,629,566 B2* | 12/2009 | Misawa ............ H01L 27/14623 |
| | | 250/208.1 |
| 2007/0291325 A1* | 12/2007 | Toyota ................ H01L 27/3234 |
| | | 358/474 |
| 2016/0081626 A1 | 3/2016 | Takahashi |

FOREIGN PATENT DOCUMENTS

| JP | H10-038683 A | 2/1998 |
| JP | 2000-332228 A | 11/2000 |
| JP | 3208538 B2 | 9/2001 |
| JP | 2006-332226 A | 12/2006 |
| JP | 2013-201309 A | 10/2013 |
| JP | 6020719 B2 | 11/2016 |

* cited by examiner

*Primary Examiner* — Que Tan Le
(74) *Attorney, Agent, or Firm* — Oliff PLC

(57) ABSTRACT

A light receiving element includes a silicon substrate, a photodiode, an amplifier circuit adapted to amplify an output signal from the photodiode, and a light blocking section adapted to cover at least a part of the amplifier circuit to block light, and the photodiode, the amplifier circuit and the light blocking section are provided to the silicon substrate.

25 Claims, 12 Drawing Sheets

LIGHT RECEIVING ELEMENT HAVING LIGHT BLOCKING SECTION COVERING AT LEAST PART OF AMPLIFIER CIRCUIT, LIGHT RECEIVING MODULE, PHOTOELECTRIC SENSOR AND BIOLOGICAL INFORMATION MEASUREMENT

CROSS-REFERENCES TO RELATED APPLICATIONS

This application claims priority to Japanese Patent Application No. 2018-061293, filed on Mar. 28, 2018, the entirety of which is herein incorporated by reference.

The present application is based on, and claims priority from JP Application Serial Number 2018-061293, filed Mar. 28, 2018, the disclosure of which is hereby incorporated by reference herein in its entirety.

BACKGROUND

1. Technical Field

The present disclosure relates to a light receiving element, a light receiving module, a photoelectric sensor and a biological information measurement device.

2. Related Art

In the past, there has been known a photo IC having a photodiode formed on a silicon substrate (see, e.g., JP-A-2006-332226 (Document 1)).

The photo IC described in Document 1 is a chip having a photodiode and a photodiode attached with an infrared transmissive filter, and first through fourth amplifier circuits formed on the silicon substrate.

The photodiode not attached with the infrared transmissive filter is coupled to an input terminal of the first amplifier circuit, the photodiode attached with the infrared transmissive filter is coupled to an input terminal of the second amplifier circuit, and signals from the respective photodiodes are amplified by the corresponding amplifier circuits. Further, the first amplifier circuit and the second amplifier circuit are coupled to the third amplifier circuit, and further, the fourth amplifier circuit is disposed in the posterior stage. The signals amplified by the first amplifier circuit and the second amplifier circuit are taken out from an output terminal via the third amplifier circuit and the fourth amplifier circuit.

In the photo IC described in Document 1, if light enters the amplifier circuit, there is a possibility that the amplifier circuit malfunctions. In particular, in the photo IC, the amplifier circuit for amplifying the output signal from the photodiode is located near to the photodiode. Therefore, there is a high possibility that a part of the light with which the photo IC is irradiated enters the amplifier circuit, and there is a possibility that a malfunction of the amplifier circuit occurs due to the incidence of the light.

Due to such a problem, there has been demanded a configuration of a light receiving element in which a malfunction is difficult to occur.

SUMMARY

An advantage of some aspects of the present disclosure is to provide a light receiving element, a light receiving module, a photoelectric sensor and a biological information measurement device capable of preventing the malfunction from occurring.

Alight receiving element according to a first aspect of the present disclosure includes a silicon substrate, a photodiode, an amplifier circuit adapted to amplify an output signal from the photodiode, and a light blocking section adapted to cover at least a part of the amplifier circuit to block light, and the photodiode, the amplifier circuit and the light blocking section are provided to the silicon substrate.

According to such a configuration, the light entering the amplifier circuit is blocked by the blocking section. According to this configuration, it is possible to prevent the light from entering the amplifier circuit. Therefore, it is possible to prevent a malfunction of the amplifier circuit from occurring.

In the first aspect described above, the light blocking section may include an aluminum layer.

According to such a configuration, it is possible to constitute the light blocking section with a relatively simple configuration. Further, in the case of forming an interconnection section of at least one of the photodiode and the amplifier circuit on the silicon substrate using an aluminum layer, it is possible to provide the light blocking section to the light receiving element in substantially the same procedure. Therefore, compared to the case of forming the light blocking section with other materials, it is possible to easily and simply form the light blocking section.

In the first aspect described above, the silicon substrate may have a first surface on which the photodiode and the amplifier circuit are disposed, the amplifier circuit may have a p-n junction part on the first surface, and an end part of the light blocking section may be located between the p-n junction part and the photodiode in a cross-sectional view from a direction perpendicular to a normal line of the first surface.

Here, there is a possibility that a part of the light entering the light receiving element circumvents the end part of the light blocking section due to diffraction or the like, and then proceeds toward the amplifier circuit. Further, if the light enters the p-n junction part provided to the amplifier circuit, there is a possibility that the electrical current occurs due to the photovoltaic effect to cause the malfunction in the amplifier circuit.

To cope with the above, according to the configuration described above, the end part of the light blocking section is located between the p-n junction part provided to the amplifier circuit and the photodiode in the cross-sectional view described above. According to this configuration, it is possible to reduce the possibility that the light circumventing the light blocking section enters the p-n junction part, and it is possible to prevent an unintended electric current from occurring in the p-n junction part. Therefore, it is possible to prevent the malfunction of the amplifier circuit.

In the first aspect described above, a distance from the end part of the light blocking section to the p-n junction part may be 100 µm or more and 300 µm or less viewed from a normal direction of the first surface.

For example, the distance described above can be set to 100 µm if the assumed intensity of the light entering the light receiving element is lower than 1,000 lux, 200 µm if lower then 10,000 lux, or 300 µm if no lower than 10,000 lux.

According to such a configuration, it is possible to prevent the light from circumventing the end part of the light blocking section to enter the p-n junction part of the amplifier circuit. Therefore, it is possible to more effectively prevent the malfunction of the amplifier circuit.

Further, since the distance described above does not exceed 300 µm, it is possible to dispose the amplifier circuit in the vicinity of the photodiode. Thus, it is possible to prevent the output signal of the photodiode to be input to the amplifier circuit from attenuating, and it is possible to amplify the output signal of the photodiode with the amplifier circuit.

In the first aspect described above, the light receiving element may further include a blocking section disposed between the photodiode and the amplifier circuit in the silicon substrate, and adapted to block an electron migrating in the silicon substrate toward the amplifier circuit.

Here, among the holes and the electrons generated in the p-n junction part of the photodiode, the holes gather in the p-layer, and the electrons gather in the n-layer. There is a possibility that the electrons (charges) gathering in the n-layer migrate in the silicon substrate to reach the p-n junction part of the amplifier circuit. In this case, an electric current occurs to make the amplifier circuit malfunction. In particular, if the photodiode and the amplifier circuit are located close to each other, there rises the possibility that the electron generated in the p-n junction part of the photodiode reaches the p-n junction part of the amplifier circuit.

To cope with the above, according to the configuration described above, the electrons migrating in the silicon substrate toward the amplifier circuit can be blocked by the blocking section. Thus, it is possible to prevent the electrons migrating from, for example, the photodiode toward the amplifier circuit from reaching the p-n junction part of the amplifier circuit. Therefore, it is possible to more effectively prevent the malfunction of the amplifier circuit.

In the first aspect described above, the blocking section may be a diode to be connected to ground of the amplifier circuit.

According to such a configuration, the blocking section can easily and simply be formed, and in addition, it is possible to block the electrons migrating in the silicon substrate toward the amplifier circuit. Therefore, it is possible to more effectively prevent the malfunction of the amplifier circuit.

In the first aspect described above, the amplifier circuit may include a charge-voltage conversion circuit adapted to convert a charge output from the photodiode into a voltage, the charge-voltage conversion circuit may include a transistor a gate of which is connected to an anode of the photodiode and a constant current source to be connected to a drain of the transistor, and the light blocking section may cover at least an area between the anode and the gate.

According to such a configuration, since the amplifier circuit includes the charge-voltage conversion circuit described above, it is possible to amplify the output signal from the photodiode. Further, since the light blocking section covers the area between the anode of the photodiode and the gate of the transistor, it is possible to prevent the light from entering the p-n junction part of the transistor. Therefore, it is possible to prevent the malfunction of the amplifier circuit from occurring.

In the first aspect described above, the amplifier circuit may include a current-voltage conversion circuit adapted to convert an electric current output from the photodiode into a voltage, the current-voltage conversion circuit may include an operational amplifier having an inverting input terminal to which an anode of the photodiode is connected, a non-inverting input terminal to be connected to ground, and an output terminal from which the output signal converted is output and a resistor and a capacitor each disposed in parallel to the operational amplifier, and the light blocking section may cover at least an area between the anode and the inverting input terminal.

According to such a configuration, since the amplifier circuit includes the current-voltage conversion circuit described above, it is possible to amplify the output signal from the photodiode. Further, since the light blocking section covers the area between the anode of the photodiode and the inverting input terminal of the operational amplifier, it is possible to reduce the influence of the light on the amplifier circuit, and in addition, it is possible to reduce the influence of the light on the output signal of the photodiode to be input to the inverting input terminal.

Alight receiving module according to a second aspect of the present disclosure includes the light receiving element described above, a processing circuit adapted to process a signal output from the light receiving element, and a board on which the light receiving element and the processing circuit are disposed.

According to such a configuration, substantially the same advantages as those of the light receiving element according to the first aspect described above can be obtained. Besides the above, since the output signal from the light receiving element is an amplified signal, the influence of the signal attenuation in the circuit can be reduced, and therefore, it is possible to increase the degree of freedom of the layout of the processing circuit on the board.

A photoelectric sensor according to a third aspect of the present disclosure includes the light receiving module described above and a light emitting element to be disposed on the board.

According to such a configuration, substantially the same advantages as those of the light receiving module according to the second aspect described above can be obtained.

In the third aspect described above, a distance between the light emitting element and the photodiode may be shorter than a distance between the light emitting element and an input region of an output signal from the photodiode in the amplifier circuit.

It should be noted that the input region is, for example, a region where the gate of the transistor to which the anode of the photodiode is connected is disposed in the charge-voltage conversion circuit described above, and in the current-voltage conversion circuit described above, there can be cited the region where the inverting input terminal of the operational amplifier to which the anode of the photodiode is connected is disposed.

According to such a configuration, it is possible to make it easy to make the light emitted from the light emitting element to the detection target, and then reflected by the detection target enter the photodiode. Thus, it is possible to improve the detection sensitivity of the light by the photoelectric sensor. Further, since the amplifier circuit is installed at the position farther from the light emitting element than the photodiode, it is possible to reduce the influence of the light emitted from the light emitting element on the amplifier circuit (in particular on the input region described above).

In the third aspect described above, the amplifier circuit may be disposed in a direction from the photodiode, the direction being perpendicular to a direction from the photodiode toward the light emitting element.

According to such a configuration, the distance between the light emitting element and the photodiode can be made shorter than the distance between the light emitting element and the input region described above of the amplifier circuit. Therefore, it is possible to improve the detection sensitivity of the light by the photoelectric sensor, and in addition, it is possible to reduce the influence of the light emitted from the light emitting element on the amplifier circuit.

In the third aspect described above, the amplifier circuit may be disposed at a position on an opposite side to the light emitting element with respect to the photodiode.

According to such a configuration, similarly to the above, the distance between the light emitting element and the photodiode can be made shorter than the distance between the light emitting element and the input region described above of the amplifier circuit. Therefore, it is possible to improve the detection sensitivity of the light by the photoelectric sensor, and in addition, it is possible to reduce the influence of the light emitted from the light emitting element on the amplifier circuit.

In the third aspect described above, the light receiving element may further include a shield section disposed between the light emitting element and the photodiode, and adapted to block light directly entering the photodiode from the light emitting element.

According to such a configuration, it is possible to further improve the detection accuracy of the light by the photoelectric sensor.

A biological information measurement device according to a fourth aspect of the present disclosure includes the photoelectric sensor described above, and a processing section adapted to determine the biological information based on a signal output from the photoelectric sensor.

According to such a configuration, substantially the same advantages as those of the photoelectric sensor according to the third aspect described above can be obtained. Further, thus, it is possible to prevent the malfunction from occurring in the amplifier circuit, and therefore, it is possible to measure the biological information high in reliability. Therefore, it is possible to improve the measurement accuracy of the biological information.

DESCRIPTION OF EXEMPLARY EMBODIMENTS

First Embodiment

A first embodiment of the present disclosure will hereinafter be described based on the drawings.

Schematic Configuration of Biological Information Measurement Device

Figure 1:
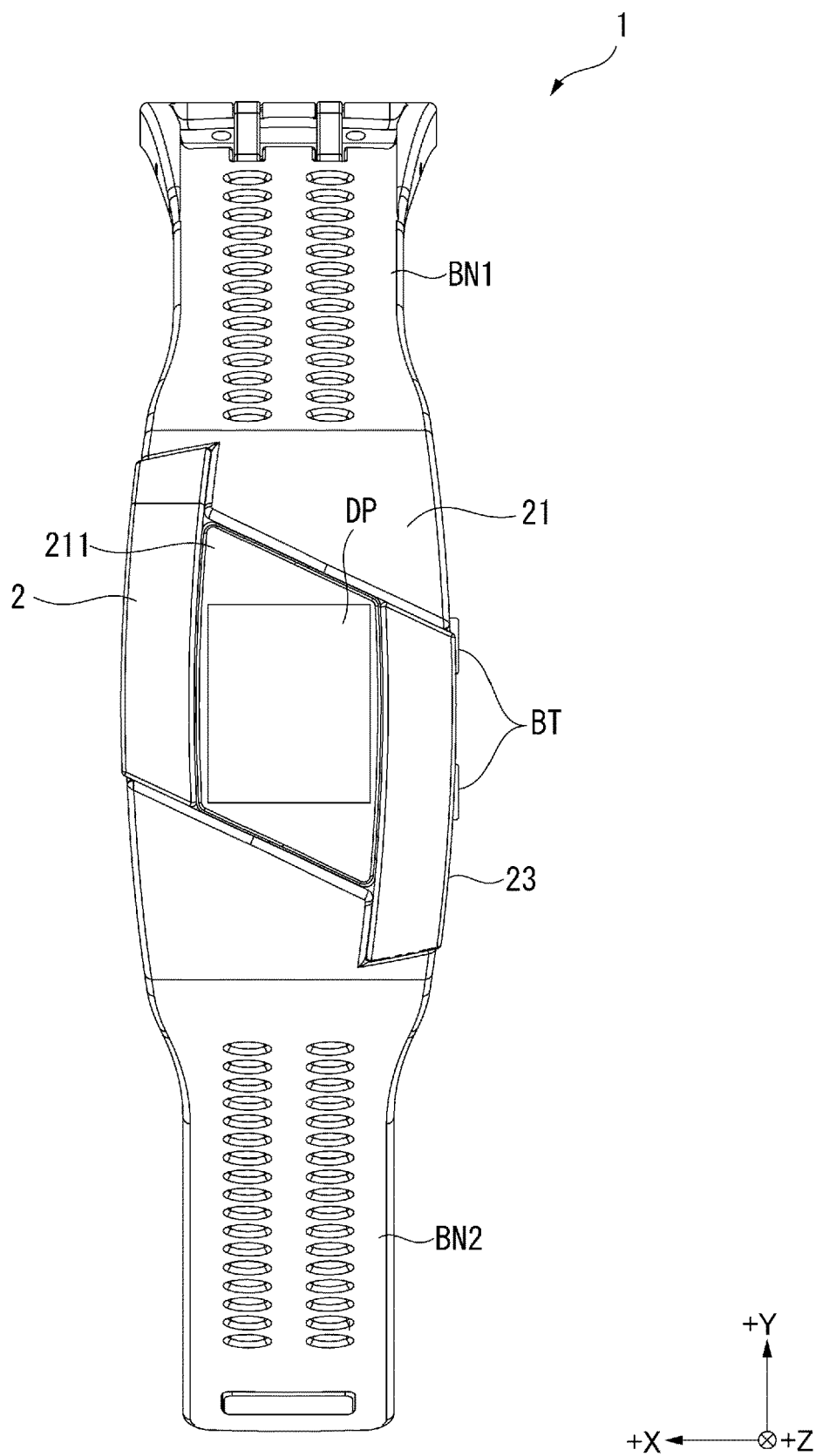
FIG. 1 is a front view showing a biological information measurement device according to a first embodiment of the present disclosure.

FIG. 1 is a front view showing a biological information measurement device according to the present embodiment.

The biological information measurement device 1 (hereinafter abbreviated as a measurement device 1 in some cases) according to the present embodiment is wearable equipment used attached to a body (living body) of the user, and measures the biological information of the user. Specifically, the measurement device 1 is used mounted on a mounting target region such as a wrist of the user, detects the pulse wave of the user as a type of the biological information to measure the pulse rate as another type of the biological information. Although the details will be described later, one of the features provided to the measurement device 1 is the configuration of a biological information detection sensor 6A.

As shown in FIG. 1, the measurement device 1 is provided with a housing 2 and bands BN1, BN2. The housing 2 is provided with a back side part 22 having contact with the body of the user when the measurement device 1 is mounted, and a front side part 21 having a display window for making the user capable of visually recognizing the biological information thus measured.

Configuration of Bands

The band BN1 extends from one end part of the housing 2, and the band BN2 extends from the other end part of the housing 2. In other words, the bands BN1, BN2 extend from the end parts opposite to each other in the housing 2 in respective directions of getting away from each other. The housing 2 is mounted on the mounting target region by the bands BN1, BN2 being coupled to each other with a clasp (not shown). It should be noted that it is also possible for the bands BN1, BN2 to be integrally formed with the housing 2.

In the following description, a direction from the front side part 21 toward the back side part 22 of the housing is defined as a +Z direction. Further, directions perpendicular to the +Z direction, and perpendicular to each other are defined as a +X direction and a +Y direction. Further, although not shown in the drawings, a −Z direction, a −X direction and a −Y direction are opposite directions of the +Z direction, the +X direction and the +Y direction, respectively.

In the present embodiment, viewing the +Y direction from the −Z direction side, the extending direction of the band BN1 is defined as the +Y direction. Further, viewing the measurement device 1 from the −Z direction side so that the +Y direction corresponds to upper side, the +X direction is defined as a direction proceeding from the right side toward the left side.

Among these directions, the +Z direction is also a direction in which the light emitting element 65 constituting a sensor section 64 of the biological information detection sensor 6 described later mainly emitting light, and is also a direction along the normal line of a surface 71A in a silicon substrate 71 of the light receiving element 7 similarly constituting the sensor section 64.

It should be noted that in the following description, viewing an object from the +Z direction side is referred to as a "planar view."

Configuration of Housing

The housing 2 has the front side part 21, the back side part 22 (see FIG. 2) and a lateral side part 23.

The front side part 21 has a light transmissive cover 211 for making the user wearing the measurement device 1 capable of visually recognizing the display section DP disposed inside the housing 2.

The lateral side part 23 has a pair of buttons BT constituting an operation section in a region on the −X direction side.

Figure 2:
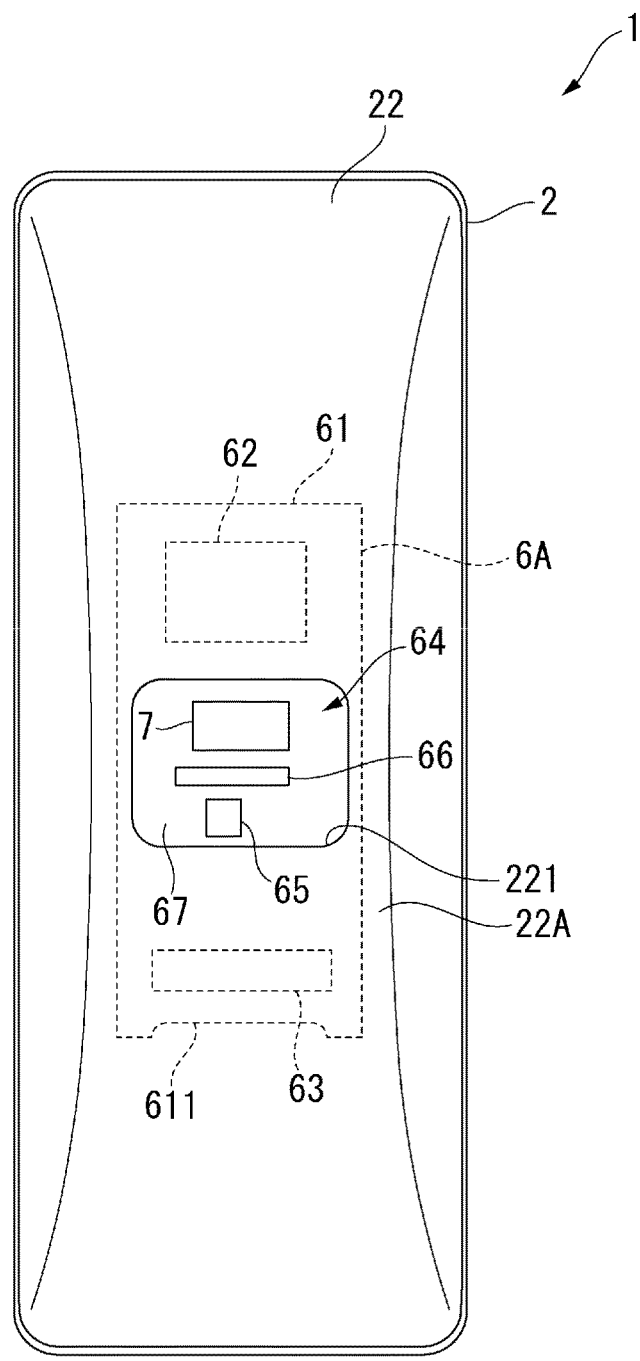
FIG. 2 is a diagram showing a back side part of the biological information measurement device in the first embodiment described above.

FIG. 2 is a diagram showing the back side part 22 of the measurement device 1.

As shown in FIG. 2, the back side part 22 has a contact surface 22A which is a surface on the +Z direction side in the back side part 22, and has contact with the living body (the body of the user) in the housing 2 when the measurement device 1 is worn by the user.

The contact surface 22A is formed to have a warped shape in which a central side bulges toward the +Z direction compared to outer edge sides. At the center of the contact surface 22A, there is formed an opening part 221 for externally exposing a sensor section 64 of the biological information detection sensor 6A housed inside the housing 2. It should be noted that the biological information detection sensor 6A will be described later in detail.

Internal Configuration of Housing

Figure 3:
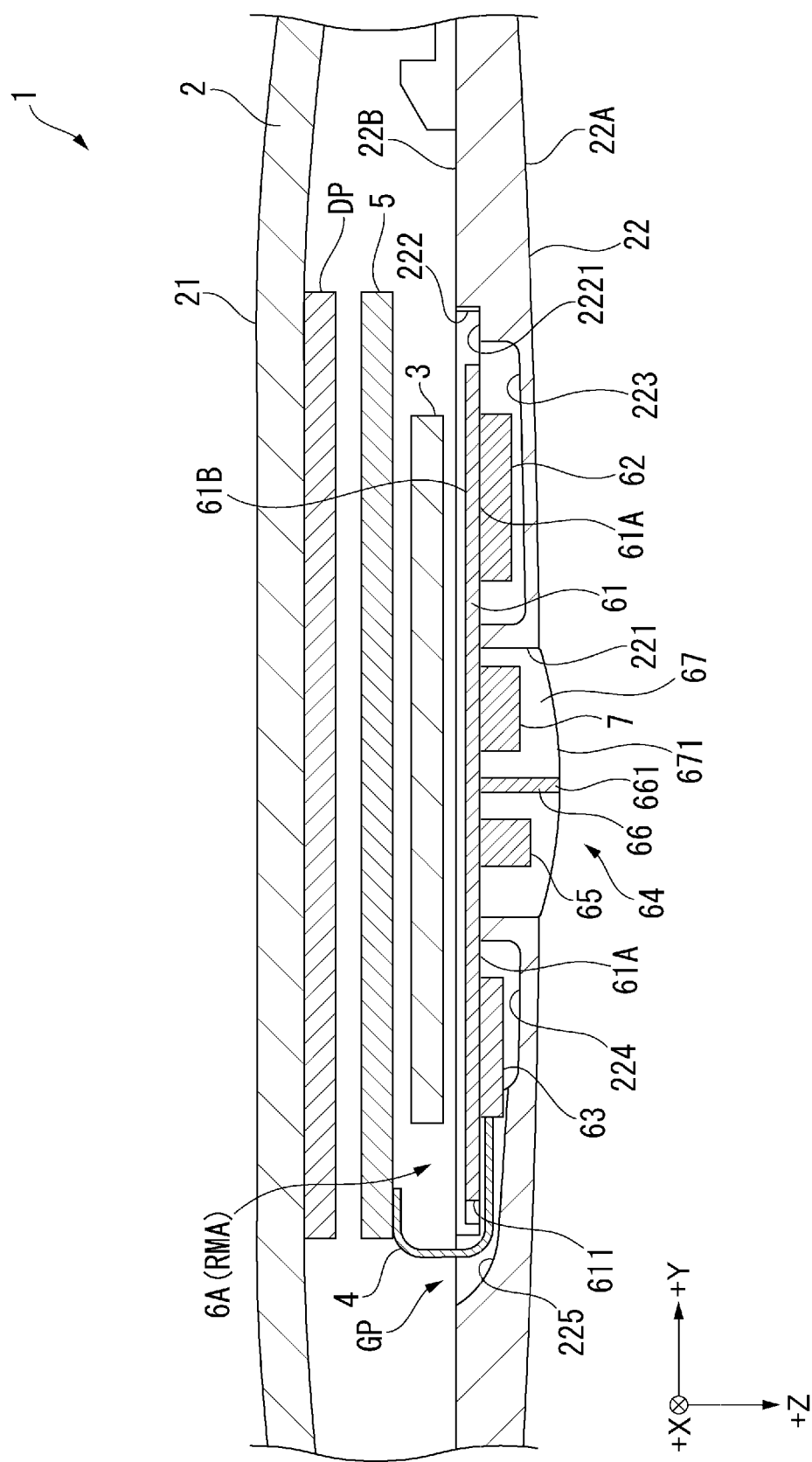
FIG. 3 is a diagram showing an internal configuration of the biological information measurement device in the first embodiment described above.

FIG. 3 is a diagram showing an internal configuration of the measurement device 1, and is in detail a diagram of a cross-section parallel to the Y-Z plane and passing through the center of the measurement device 1 viewed from the −X direction side.

The measurement device 1 has a battery 3, a coupling member 4, a circuit board 5 and the biological information detection sensor 6A each housed in the housing 2 as shown in FIG. 3 besides the above.

The battery 3 is located between the circuit board 5 and the biological information detection sensor 6A in the +Z direction, and supplies electricity for operating the measurement device 1. In the present embodiment, the battery is a secondary cell charged by electricity externally supplied under the control by the circuit board 5. However, this is not a limitation, and the battery 3 can also be a primary cell.

The coupling member 4 is a member for electrically coupling the circuit board 5 and the biological information detection sensor 6A to each other. The coupling member 4 is formed of flexible printed circuits (FPC) in the present embodiment, but can also be a conductive member such as a cable or a harness.

Configuration of Circuit Board

The circuit board 5 is a control board for controlling the whole of the measurement device 1, and has a configuration in which a plurality of circuit elements is disposed on a rigid board although the detailed illustration is omitted. As such circuit elements, the circuit board 5 as an acceleration sensor, a wireless communication circuit, a display control circuit, a storage circuit and a control circuit.

The acceleration sensor detects the acceleration acting on the measurement device 1 to output a signal representing the acceleration thus detected to the control circuit as a body motion signal representing the body motion of the user. It should be noted that the body motion signal is also used for removal of the body motion noise included in a pulse wave signal. The removal of the body motion noise is performed when the control circuit analyzes the pulse wave signal to determine the pulse rate.

The wireless communication circuit transmits the biological information and the body motion information based on the detection result of the biological information detection sensor 6A and the acceleration sensor to external equipment, and in addition, outputs the information received from the external equipment to the control circuit under the control by the control circuit.

The display control circuit displays predetermined information on a display section DP under the control by the control circuit. For example, the display control circuit displays the pulse rate analyzed by the control circuit on the display section DP.

The storage circuit is formed of a nonvolatile memory such as a flash memory, and stores programs and data necessary for the operation of the measurement device 1. Besides the above, the storage circuit stores the detection result by the biological information detection sensor 6A and the acceleration sensor, and the analysis result by the control circuit.

The control circuit is constituted by an arithmetic processing circuit such as a central processing unit (CPU), and controls the whole of the measurement device 1 autonomously or in accordance with an input operation of the user to the operation section such as the buttons BT. For example, the control circuit determines the biological information based on the detection result by the biological information sensor 6A and the acceleration sensor. In the present embodiment, the control circuit determines the pulse rate as a type of biological information of the user based on the pulse wave signal input from the biological information detection sensor 6A and the body motion signal input from the acceleration sensor. In other words, the control circuit functions as a processing section.

Further, the control circuit stores the pulse rate thus determined in the storage circuit, and in addition, displays the pulse rate on the display section DP or transmits the pulse rate to the external equipment with the wireless communication circuit if needed.

Configuration of Biological Information Detection Sensor

The biological information detection sensor 6A is a reflective photoelectric sensor, and is used for a biological information measurement device for measuring the biological information such as the measurement device 1. In the detailed description, the biological information detection sensor 6A irradiates the living body (e.g., the body of the user) with the light, and then outputs a signal representing a variation in reception intensity of the reflected light reflected by the living body as the signal (e.g., the pulse wave signal) representing the biological information.

The biological information detection sensor 6A has a board 61, a processing circuit 62, a connector 63 and the sensor section 64.

Configuration of Board

The board 61 is a board which is provided with the processing circuit 62, the connector 63 and the sensor section 64 disposed on a mounting surface 61A as a surface on the +Z direction side, and supports these constituents. The shape of the board 61 in a planar view is a roughly rectangular shape longer in the +Y direction and shorter in the +X direction, but can arbitrarily be changed. Further, the board 61 is a rigid board in the present embodiment, but can also be an FPC.

The board 61 has a recessed part 611 recessed toward the +Y direction in an end part on the −Y direction side. The recessed part 611 forms a gap GP through which the coupling member 4 described above is inserted with a recessed part 225 described later.

Such a board 61 is disposed in an installation part 222 having a recessed shape recessed toward the +Z direction from an inner surface 22B on the −Z direction side in the back side part 22 so that the mounting surface 61A faces to the +Z direction side.

It should be noted that no circuit element is disposed on a reverse surface 61B on the opposite side to the mounting surface 61A in the board 61. However, it is also possible to dispose a circuit element having a predetermined function on the reverse surface 61B.

Configuration of Processing Circuit

The processing circuit 62 is disposed inside a recessed part 223 further recessed toward the +Z direction side from the bottom part 2221 of the installation part 222 described above so as to be located on the +Y direction side with respect to the sensor section 64. The processing circuit 62 has a part of a function of a so-called analog front end (AFE), and processes an output signal of the light receiving element 7 constituting the sensor section 64. Specifically, the processing circuit 62 performs processes such as noise removal, secondary amplification and A/D conversion on the output signal of the light receiving element 7. In other words, the processing circuit 62 has a filter section, an amplifying section, an A/D conversion section and a communication section. Then, the processing circuit 62 outputs the signal thus processed to the connector 63.

Configuration of Connector

The connector 63 is located on the −Y direction side with respect to the sensor section 64. The connector 63 functions as a coupling section to be coupled to the coupling member 4, and outputs the signal processed by the processing circuit 62 to the circuit board 5 via the coupling member 4.

It should be noted that the connector 63 is disposed inside a recessed part 224 further recessed toward the +Z direction from the bottom part 2221 of the installation part 222 described above. The recessed part 224 is coupled to the recessed part 225 recessed toward the −Y direction in the installation part 222. Further, the coupling member 4 one end of which is coupled to the connector 63 passes through the gap GP between the recessed part 611 and the recessed part 225, and is coupled to the circuit board 5 in the other end.

Configuration of Sensor Section

The sensor section 64 is located at roughly the center of the contact surface 22A in the back side part 22, and performs irradiation of the living body with the light and reception of the light reflected by the living body to output the signal corresponding to the reception intensity as the signal (e.g., the pulse wave signal) representing the biological information.

As shown in FIG. 2 and FIG. 3, the sensor section 64 has a light emitting element 65 for emitting light, the light receiving element 7 for receiving the light via the living body, a shield section 66 and a sealing section 67 (FIG. 3).

Among these constituents, the light receiving element 7 will be described later in detail. It should be noted that the board 61, the processing circuit 62 and the light receiving element 7 of the sensor section 64 constitute a light receiving module RMA (FIG. 3) according to the present disclosure.

The light emitting element 65 emits the light (detection light, e.g., green light) with which the living body is irradiated. Although the detailed illustration will be omitted, the light emitting element 65 has a semiconductor element such as a light emitting diode (LED), a cover part for covering the light emitting element so as to surround the light emitting element, and a lens provided to the cover part. In other words, the light emitting element 65 is a packaged LED chip.

Among these, the cover part has a reflecting section surrounding the semiconductor element from four directions (the ±X directions and the ±Y directions) in the planar view, and light transmissive sealing resin with which a gap between the semiconductor element and the reflecting section is filled. Out of the light emitted from the semiconductor element, the light emitted toward the ±X direction and the ±Y direction is reflected by the reflecting section toward the +Z direction, and enters the lens. It should be noted that the light emitted from the semiconductor element toward the +Z direction also enters the lens. The light emitted from the semiconductor element and then enters the lens in such a manner is collected by the lens and is then emitted.

The shield section 66 is disposed between the light emitting element 65 and the light receiving element 7, and blocks the light emitted from the light emitting element 65 and directly proceeding toward the light receiving element 7 without the intervention of the living body. It should be noted that in the present embodiment, the shield section 66 is formed of a plate-like member disposed between the light emitting element 65 and the light receiving element 7 as a light blocking wall. However, this is not a limitation, and it is also possible for the shield section 66 to be formed to have a ring-like shape or a polygonal shape surrounding the light receiving element 7 in the planar view.

As shown in FIG. 3, the sealing section 67 seals the light emitting element 65, the light receiving element 7 and the shield section 66 on the mounting surface 61A to protect the light emitting element 65, the light receiving element 7 and the shield section 66. The sealing section 67 is exposed to the outside of the housing 2 via the opening part 221 of the back side part 22. Therefore, the sealing section 67 is formed to have a shape coinciding with the opening part 221 viewed from the +Z direction side.

The sealing section 67 is formed of the light transmissive resin (sealing resin) for transmitting the light emitted from the light emitting element 65 and the light entering the light receiving element 7.

It should be noted that sealing does not necessarily mean that the whole of the sealing target as the target of sealing is enclosed inside the sealing section 67. For example, providing the sealing section 67 encloses the light emitting element 65 and the light receiving element 7 as the sealing target inside the sealing section 67, it is also possible for apart of the shield section 66 similarly as the sealing target to slightly be exposed outside the sealing section 67.

Such a sealing section 67 has a living body contact surface 671 which is a surface on the +Z direction side, and has contact with the living body when the measurement device 1 is mounted on the living body. The living body contact surface 671 is also an emission surface from which the light having been emitted from the light emitting element 65 is emitted mainly outside the sealing section 67, and further, is also a plane of incidence through which the light entering the light receiving element 7 mainly enters the sealing section 67 from the outside (the living body). In other words, the living body contact surface 671 is an incident/emission surface with respect to the sealing section 67.

Such a living body contact surface 671 is formed to have a convexly curved surface in which the central part in the case of being viewed from the +Z direction side bulges toward the +Z direction from the outer edge side. The shape of the living body contact surface 671 is a shape calculated to collect the light emitted from the light emitting element 65 to irradiate the living body with the collected light.

Here, a tip part 661 in the projection direction (the +Z direction) from the mounting surface 61A in the shield section 66 is located between an end part on the +Z direction side in the light emitting element 65 and the living body contact surface 671. Thus, the waterproof property and the dust resistance of the measurement device 1 due to the sealing section 67 are improved.

However, this is not a limitation, and it is possible for the position of the tip part 661 to roughly coincide with the living body contact surface 671, or to be located on the +Z direction side of the living body contact surface 671. In this case, although there is a possibility that the waterproof property and the dust resistance of the measurement device 1 deteriorate, it is possible to block the light which is emitted from the light emitting element 65, and is then internally reflected by the living body contact surface 671 as the boundary face, and then directly enters the light receiving element 7.

Configuration of Light Receiving Element

Figure 4:
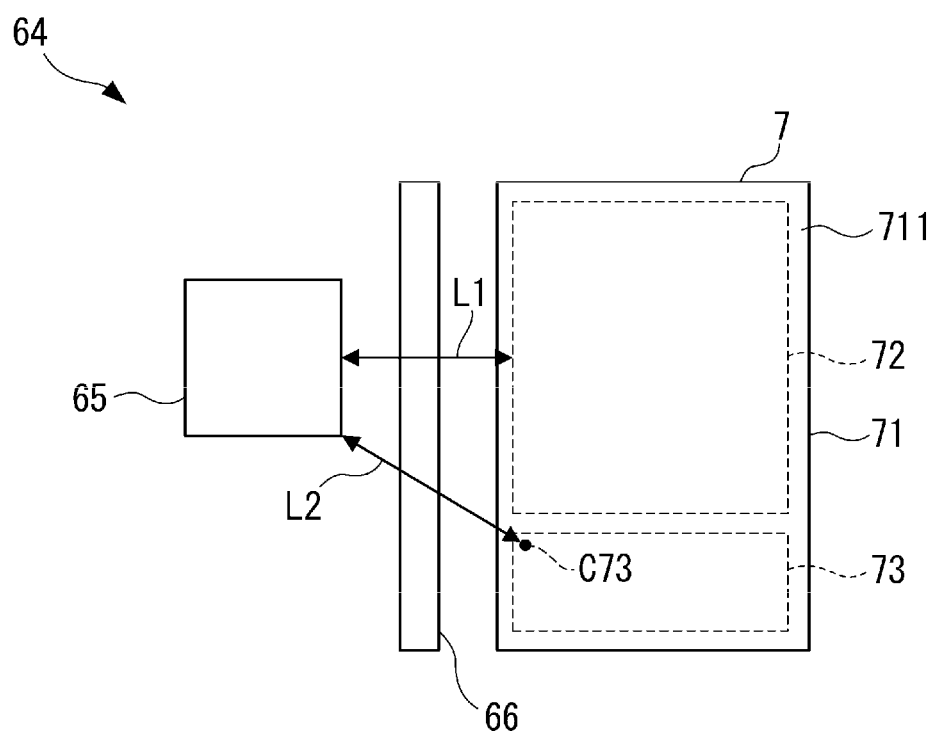
FIG. 4 is a diagram showing a configuration of a light receiving element in the first embodiment described above, and a positional relationship between the light receiving element and a light emitting element.

FIG. 4 is a diagram showing a configuration of the light receiving element 7, and a positional relationship between the light receiving element 7 and the light emitting element 65.

The light receiving element 7 receives the light reflected by the living body, then amplifies a signal corresponding to the reception intensity, and then outputs the signal thus amplified. As shown in FIG. 4, the light receiving element 7 has a silicon substrate 71, and a photodiode 72 and an amplifier circuit 73 each disposed on a surface 71A of the silicon substrate 71. In other words, the light receiving element 7 is a single chip having the photodiode 72 and the amplifier circuit 73 disposed adjacent to each other.

The silicon substrate 71 is an n-type silicon wafer formed to have a roughly rectangular shape longer in the +X direction and shorter in the +Y direction. The photodiode 72 is formed in a region on the −X direction side in the surface 71A as a first surface of the silicon substrate 71, and the amplifier circuit 73 is formed in a region on the +X direction side.

The photodiode 72 is electrically coupled to the amplifier circuit 73, and outputs the signal corresponding to the intensity of the received light to the amplifier circuit 73. The photodiode 72 is disposed in an area overlapping the light emitting element 65 in the silicon substrate 71 viewed from the +Y direction side. In contrast, the amplifier circuit 73 is disposed in an area not overlapping the light emitting element 65 in the silicon substrate 71. In other words, the amplifier circuit 73 is disposed in the +X direction from the photodiode 72, the +X direction being perpendicular to the −Y direction which is a direction from the photodiode 72 toward the light emitting element 65.

Therefore, the distance L1 between the light emitting element 65 and the photodiode 72 is shorter than the distance L2 between the light emitting element 65 and an input region C73 of the output signal from the photodiode 72 in the amplifier circuit 73. In the detailed description, the shortest distance between the light emitting element 65 and the photodiode 72 is shorter than the shortest distance between the light emitting element 65 and the input region 73C of the amplifier circuit 73.

The configuration of such a photodiode 72 will be described later in detail.

It should be noted that the position of the input region C73 shown in FIG. 4 is illustrative only, and can arbitrarily be changed. However, since the amplifier circuit 73 is disposed in the direction perpendicular to the direction from the photodiode 72 toward the light emitting element 65, the shortest distance between the light emitting element 65 and the photodiode 72 is shorter than the shortest distance between the light emitting element 65 and the input region C73 of the amplifier circuit 73 wherever the input region C73 is disposed in the amplifier circuit 73.

Figure 5:
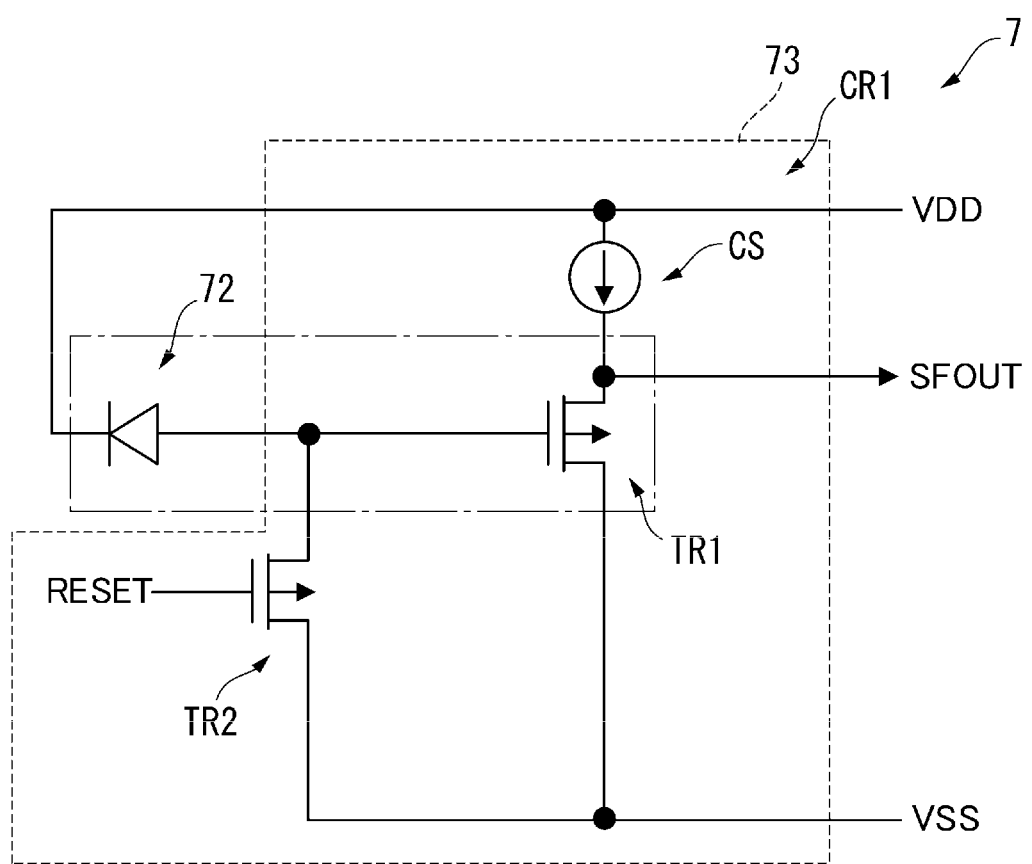
FIG. 5 is a circuit diagram showing a configuration of an amplifier circuit in the first embodiment described above.

FIG. 5 is a circuit diagram showing a configuration of the amplifier circuit 73.

The amplifier circuit 73 is an initial stage amplifier circuit for amplifying the output signal of the photodiode 72. In the present embodiment, the amplifier circuit 73 is configured including a charge-voltage conversion circuit having two transistors TR1, TR2 each of which is an N-channel MOSFET and a constant current source CS as shown in FIG. 5.

The gate of the transistor TR1 is the region corresponding to the input region C73 described above, and is coupled to the anode of the photodiode 72, the source of the transistor TR1 is coupled to Vss, and the drain of the transistor TR1 is coupled to the constant current source and SFOUT.

The gate of the transistor TR2 is coupled to a reset circuit, the source of the transistor TR2 is coupled to Vss, and the drain of the transistor TR2 is coupled to the anode of the photodiode 72 and the gate of the transistor TR1.

In the charge-voltage conversion circuit CR1, the charge output from the photodiode 72 is applied to the gate of the transistor TR1. Then, the current with the voltage corresponding to the amount of the charge applied to the gate of the transistor TR1 is output from the constant current source as an output of the charge-voltage conversion circuit CR1. Thus, the output signal of the photodiode 72 is output with the signal level amplified.

It should be noted that the reset circuit to be coupled to the gate of the transistor TR2 periodically performs a reset operation for discharging the accumulated charge.

Such a charge-voltage conversion circuit CR1 is required to discharge the accumulated charge, and is therefore difficult to speed up the charge-voltage conversion. However, in the amplification of a signal such as the pulse wave signal the signal waveform of which can be followed even if the sampling frequency is low, a sufficient speed of the charge-voltage conversion can be ensured. Besides the above, by elongating the period of the reset operation, the area of the photodiode 72 can be made small, and it is possible to achieve reduction in size of the light receiving element 7.

Structure of Light Receiving Element

Figure 6:
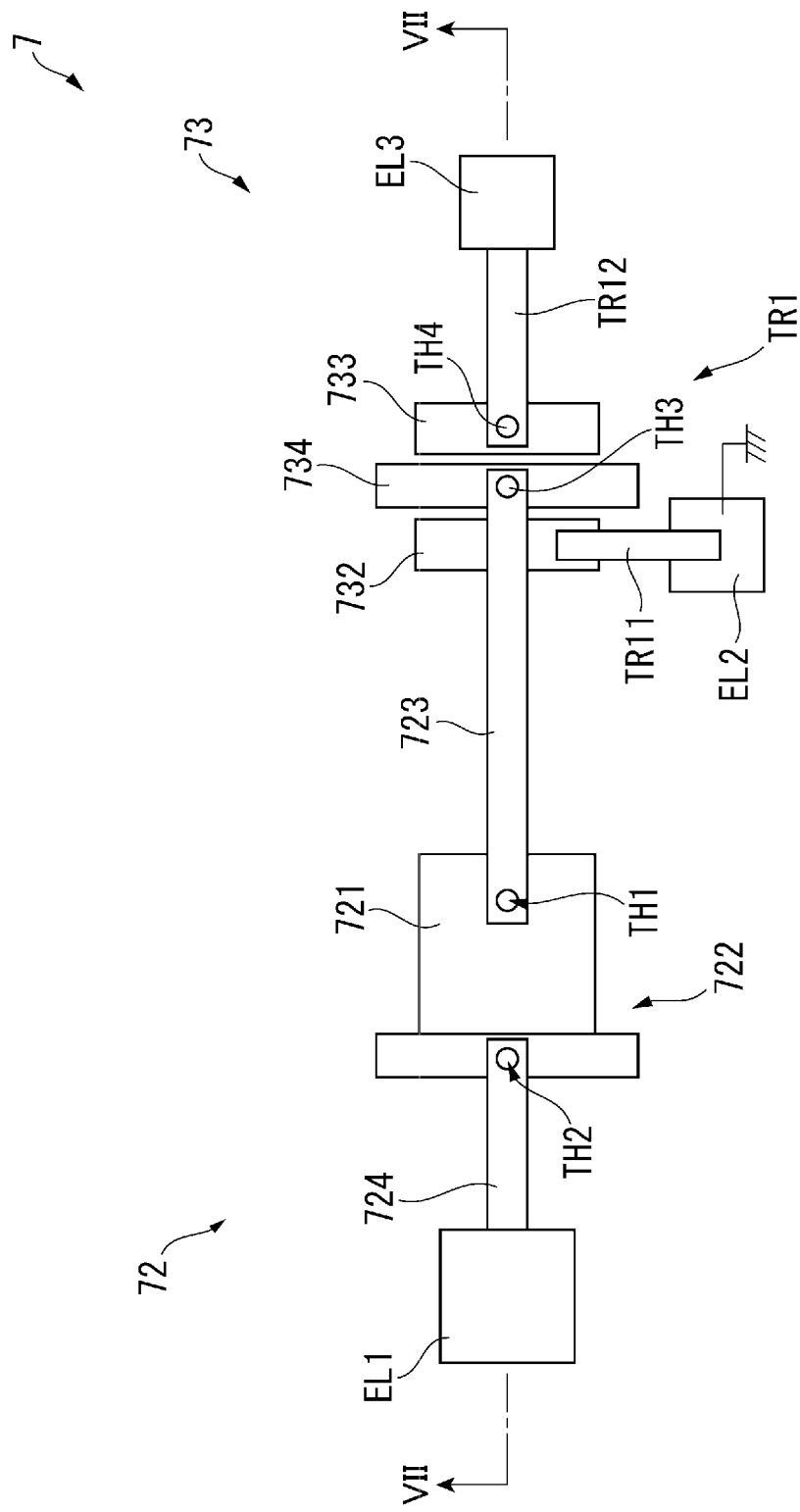
FIG. 6 is a schematic diagram showing a part of the light receiving element in the first embodiment described above in an enlarged manner.
Figure 7:
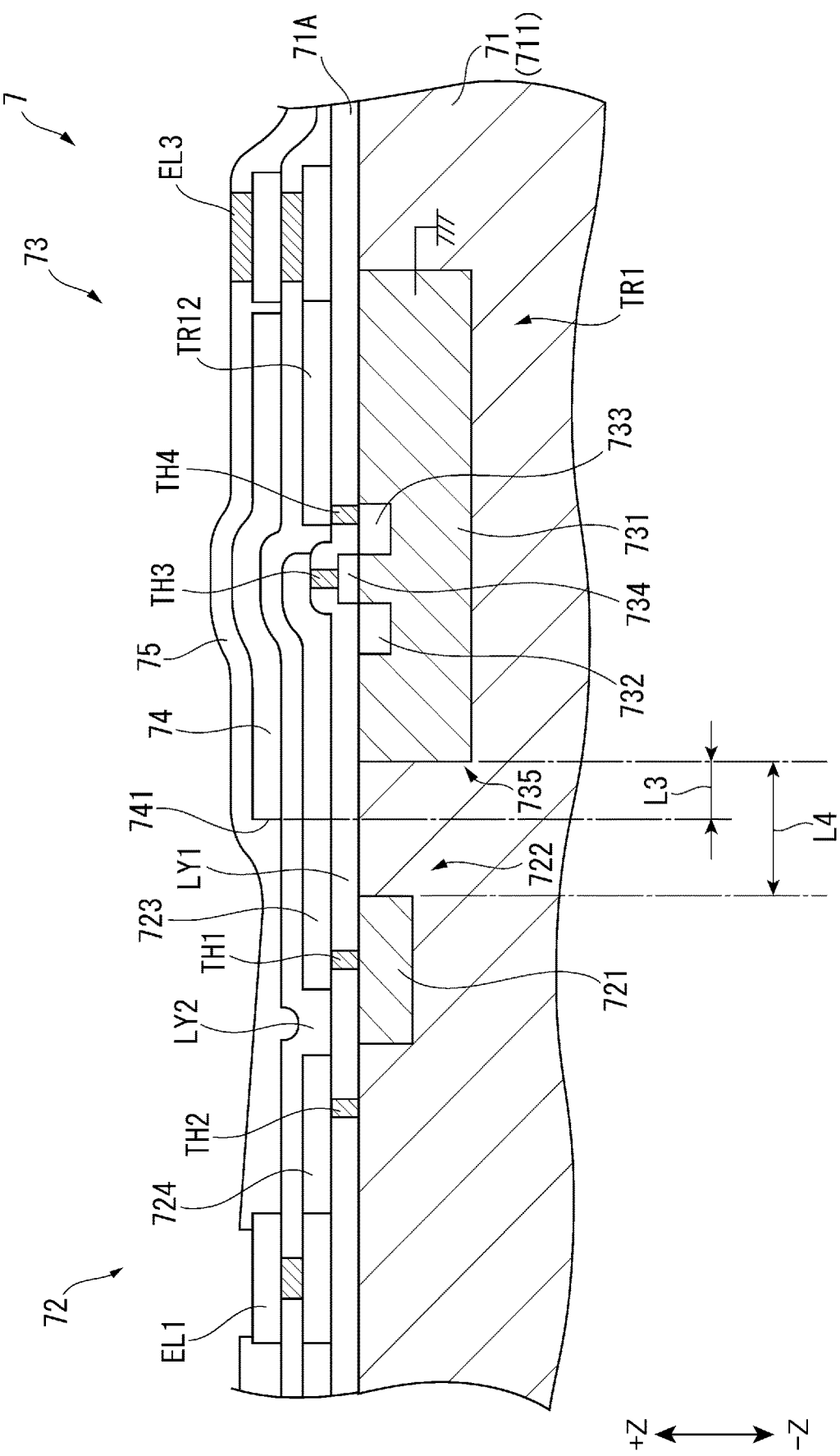
FIG. 7 is a diagram showing a cross-sectional surface of the light receiving element in the first embodiment described above.

FIG. 6 is a schematic diagram showing a part of the light receiving element 7 in an enlarged manner, and is a schematic diagram showing a configuration of the region indicated by the dashed-dotted line in FIG. 5. Further, FIG. 7 is a diagram showing a cross-section of the light receiving element 7 in the line VII-VII in FIG. 6, and is a diagram showing a layer structure of the light receiving element 7. It should be noted that in FIG. 7, some of the constituents of the light receiving element 7 are displayed in an enlarged manner to the extent that the constituents can visually be recognized.

The photodiode 72 in the present embodiment is a PN photodiode, and has a p-layer 721, an anode electrode 723 and a cathode electrode 724 formed in the silicon substrate 71 as an n-type semiconductor as shown in FIG. 6 and FIG. 7.

A p-n junction part 722 is formed between the p-layer 721 and an n-layer 711 of the silicon substrate 71.

The anode electrode 723 is formed of an aluminum layer. One end of the anode electrode 723 is coupled to the p-layer 721 via a through hole TH1 provided to a first insulating layer LY1 covering the p-layer 721. Further, the other end of the anode electrode 723 is coupled to an oxidized insulating layer 734 functioning as the gate of the transistor TR1 constituting the amplifier circuit 73.

The cathode electrode 724 is also formed of an aluminum layer. One end of the cathode electrode 724 is coupled to the n-layer 711 of the silicon substrate 71 via a through hole TH2 provided to the first insulating layer LY1. Further, the other end of the cathode electrode 724 is coupled to an electrode EL1 including a pad.

It should be noted that each of the first insulating layer LY1 and a second insulating layer LY2 is an $SiO_2$ layer having a light transmissive property in the present embodiment.

When such a photodiode 72 is irradiated with the light, an electric current is generated due to the photovoltaic effect in the p-n junction part 722, and the electric current corresponding to the reception intensity is output from the anode electrode 723 to the amplifier circuit 73.

The transistor TR1 of the amplifier circuit 73 has a p-layer 731 formed in the silicon substrate 71, two n-layers 732, 733 formed in the p-layer 731, and the oxidized insulating layer 734 covering a part of each of the two n-layers 732, 733 on the p-layer 731.

Among these, the oxidized insulating layer 734 functions as the gate of the transistor TR1. The oxidized insulating layer 734 is coupled to the anode electrode 723 of the photodiode 72 via a through hole TH3 provided to the first insulating layer LY1.

The n-layer 732 functions as the source of the transistor TR1. As shown in FIG. 6, the n-layer 732 is coupled to an electrode EL2 via a conducive layer TR11 as an aluminum layer.

The n-layer 733 functions as the drain of the transistor TR1. As shown in FIG. 6 and FIG. 7, the n-layer 733 is coupled to an electrode EL3 including a pad via a through hole TH4 provided to the first insulating layer LY1, and then via a conductive layer TR12 as an aluminum layer.

Configuration of Light Blocking Section

Here, as described above, the light receiving element 7 is a light receiving chip in which the signal output by the photodiode 72 having received the light is amplified and then output by the amplifier circuit 73. However, if the light enters the amplifier circuit 73, there is a possibility that the amplifier 73 malfunctions.

To cope with the above, the light receiving element 7 has a light blocking section 74 for covering at least a part of the amplifier circuit 73 on the +Z direction side, and a protecting section 75 for covering the light blocking section on further the +Z direction side in addition to the constituents described above as shown in FIG. 7.

The light blocking section 74 is a light blocking layer for covering the second insulating layer LY2 on the +Z direction side. The light blocking layer is an aluminum layer in the present embodiment, but can also be a light blocking layer formed of another material. It should be noted that in the case in which the light blocking layer is the aluminum layer, it is possible to form the light blocking layer in a similar formation process to those of the anode electrode 723 and the cathode electrode 724, and the conductive layers TR11, TR12, and therefore, it is possible to prevent the formation process of the light blocking layer from becoming complicated.

Configuration of Protecting Section

The protecting section 75 is a protective layer formed in a broader range than the light blocking section 74, and a part of the protecting section 75 covers not only the light blocking section 74, but also the photodiode 72 on the +Z direction side. The protecting section 75 protects the photodiode 72 and the amplifier circuit 73, and at the same time insulates the light blocking section 74 including an aluminum layer. It should be noted that the protecting section 75 can be formed of $SiO_2$ similarly to the insulating layers LY1, LY2 described above. Thus, similarly to the light blocking section 74 described above, it is possible to prevent the formation process of the protecting section 75 from becoming complicated. However, it is possible for the protecting section 75 to be formed of another material. For example, if the protecting section 75 does not cover the photodiode 72, it is also possible for the protecting section 75 to be formed of a material not having a light transmissive property. Further, in the case in which the light blocking section 74 is formed of an insulating body, and so on, the protecting section 75 can be eliminated.

Installation Position of Light Blocking Section

Figure 8:
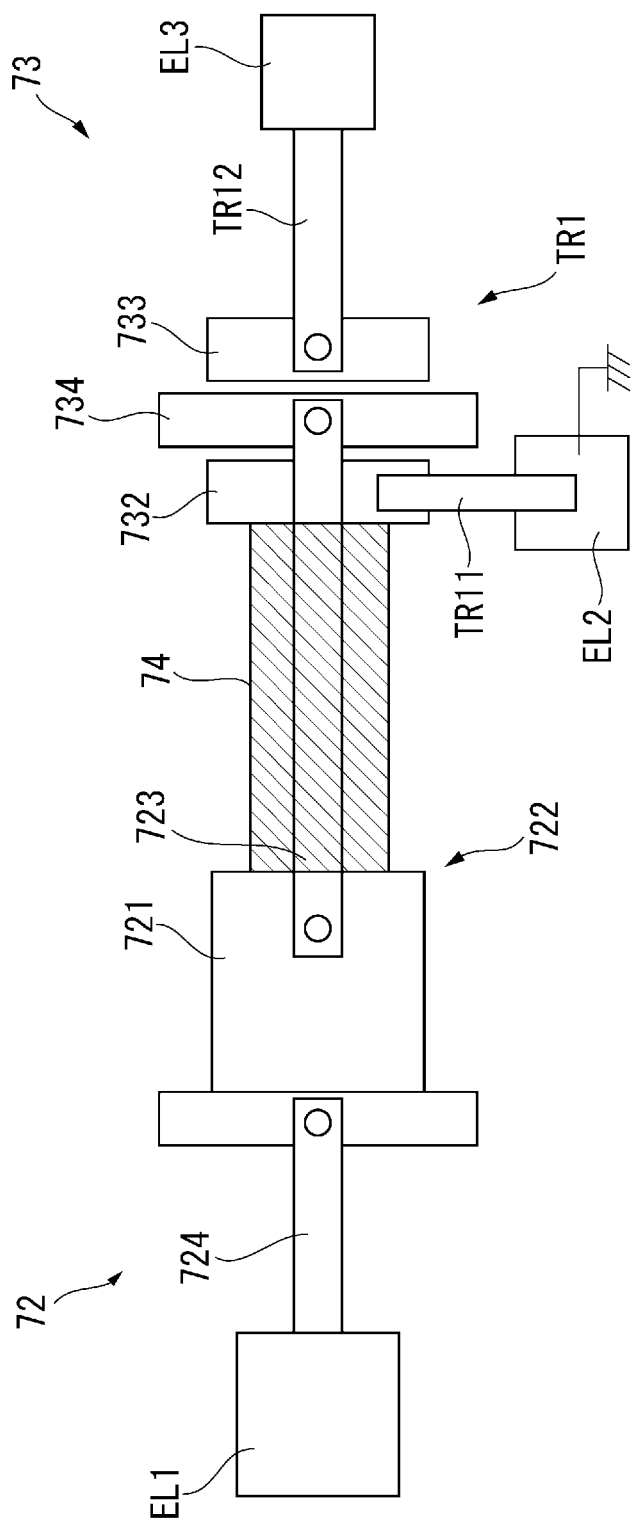
FIG. 8 is a diagram showing an example of an installation position of a light blocking section in the first embodiment described above.

FIG. 8 is a diagram showing an example of the installation position of the light blocking section 74. It should be noted that in FIG. 8, the light blocking section 74 is represented by the area provided with the hatching.

Here, the position of the light blocking section 74 will be described.

It is possible for the light blocking section 74 to set an installation range in accordance with assumed intensity of the light entering the light receiving element 7.

For example, in the case in which the assumed intensity is lower than 500 lux, it is conceivable to dispose the light blocking section 74 so as to cover the range from the output of the photodiode 72 to the gate of the transistor TR1 constituting the amplifier circuit 73 as shown in FIG. 8. Specifically, in the case in which the assumed intensity is lower than 500 lux, it is conceivable to dispose the light blocking section 74 so as to cover the range from an end part on the amplifier circuit 73 side (the transistor TR1 side) in the p-layer 721 of the photodiode 72 to an end part on the photodiode 72 side (the p-layer 721 side) in the n-layer 732 located on the photodiode 72 side of the transistor TR1. Thus, the influence of the light on the amplifier circuit 73 can be suppressed.

Even in this case, the p-n junction part 735 located between the region on the photodiode 72 side and the n-layer 711 of the silicon substrate 71 in the p-layer 731 of the transistor TR1 is covered with the light blocking section 74 as shown in FIG. 7.

Figure 9:
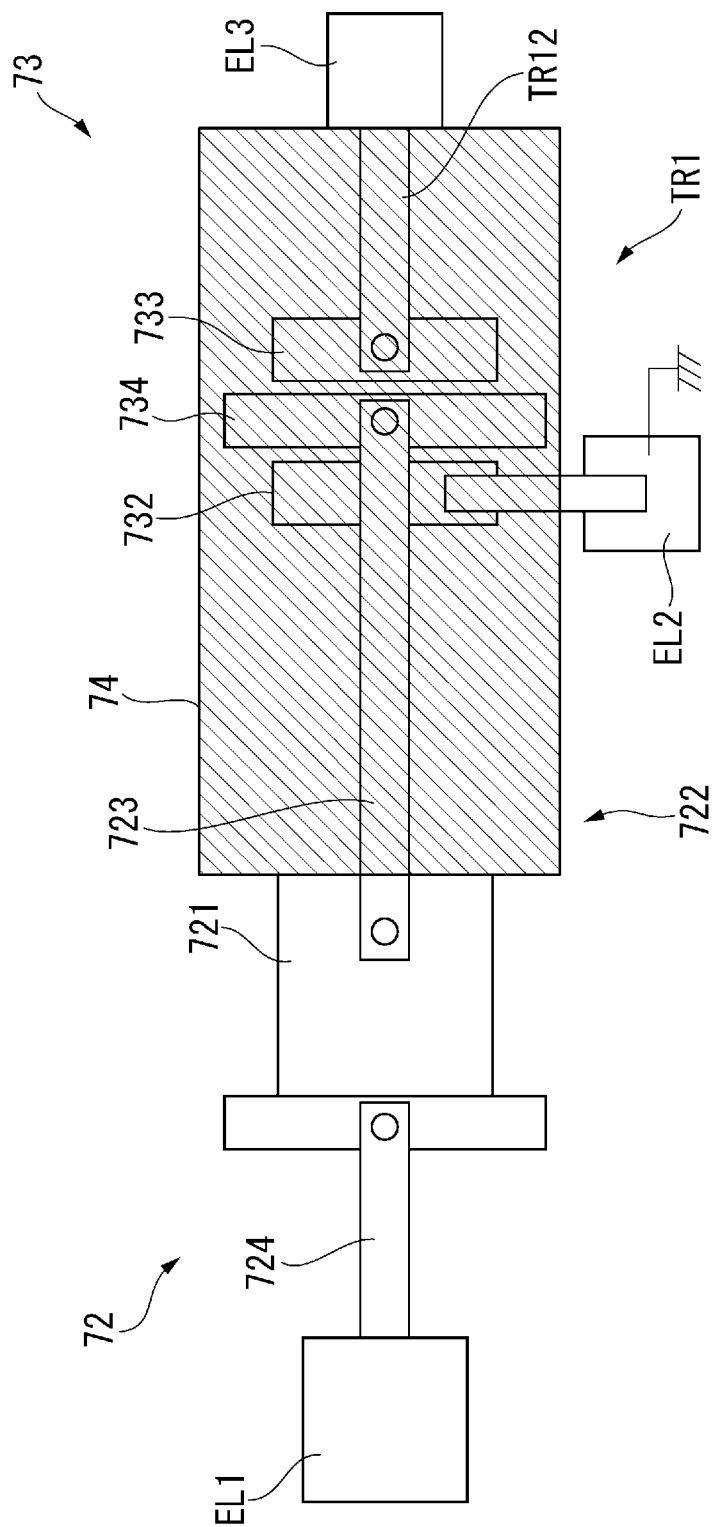
FIG. 9 is a diagram showing another example of the installation position of the light blocking section in the first embodiment described above.

FIG. 9 is a diagram showing another example of the installation position of the light blocking section 74. It should be noted that also in FIG. 9, the light blocking section 74 is represented by the area provided with the hatching.

For example, in the case in which the assumed intensity is lower than 5,000 lux, it is conceivable to dispose the light blocking section 74 so as to cover the range from the output of the photodiode 72 to the whole of the transistor TR1 as shown in FIG. 9. Specifically, in the case in which the assumed intensity is lower than 5,000 lux, it is conceivable to dispose the light blocking section 74 so as to cover the range from an end part on the amplifier circuit 73 side (the transistor TR1 side) in the p-layer 721 of the photodiode 72 to an end part on the photodiode 72 side in the electrode EL3 to be coupled to the drain of the transistor TR1.

Further, for example, in the case in which the assumed intensity is lower than 10,000 lux, it is conceivable to dispose the light blocking section 74 so as to cover the range from the output of the photodiode 72 to the whole of the amplifier circuit 73 although not shown in the drawings.

It should be noted that it is also possible to dispose a plurality of layers of light blocking section 74. For example, in the case in which the assumed intensity is no lower than 10,000 lux, it is possible to dispose the light blocking section 74 so as to cover the range from the output of the photodiode 72 to the whole of the amplifier circuit 73.

Since the aluminum layer formed on the silicon substrate is relatively small in layer thickness, the possibility that a part of the incident light passes through the aluminum layer is conceivable. In particular, in the case in which the intensity of the incident light is high such as the case in which the direct sunlight enters the aluminum layer, it is conceivable that a part of the incident light passes through the aluminum layer.

To cope with the above, by disposing a plurality of layers of light blocking section 74, the light to be transmitted can surely be reduced, and therefore, the influence of the light on the amplifier circuit 73 can surely be reduced. It should be noted that in the case of disposing the plurality of layers of light blocking section 74, it is preferable to adopt a configuration in which the protecting section 75 intervenes between the layers from the viewpoint of the insulation and the manufacture.

By disposing the light blocking section 74 in such a manner, it is possible to block the light directly entering the amplifier circuit 73, and thus, it is possible to suppress the influence of the light on the amplifier circuit 73.

Positional Relationship Between End Part of Light Blocking Section and p-n Junction Part of Amplifier Circuit Hereinabove, it is described that the light blocking section 74 is disposed so as to cover at least a part of the amplifier circuit 73. On the other hand, there is a possibility that the light entering the light receiving element 7 does not always enter the light receiving element 7 along the normal line (along the −Z direction) of the surface 71A of the silicon substrate 71, but there is a possibility that the light obliquely enters the surface 71A, and in addition, there is a possibility that the proceeding direction of the light is slightly deflected due to refraction when passing through the layered structure of the SiO$_2$ layer and so on forming the light receiving element 7 or diffraction when passing through the vicinity of the end part of the light blocking section 74. In order to reduce the influence of such light on the amplifier circuit 73, in the present embodiment, the position of the end part in the planar view of the light blocking section 74 is set in accordance with the assumed intensity of the light entering the light receiving element 7.

For example, as shown in FIG. 7, defining the distance in the planar view between the p-n junction part 735 formed of the p-layer 731 provided to the transistor TR1 and the n-layer 711 of the silicon substrate 71, and the end part 741 of the light blocking section 74 as a distance L3, the distance L3 can be set as described below in accordance with the assumed intensity.

In the case in which the assumed intensity is lower than 1,000 lux, the distance L3 can be set to 100 μm.

In the case in which the assumed intensity is lower than 10,000 lux, the distance L3 can be set to 200 μm.

In the case in which the assumed intensity is no lower than 10,000 lux, the distance L3 can be set to 300 μm.

The end part 741 of the light blocking section 74 is away from the p-n junction part 735 in a direction from the center of the p-layer 731 toward the outside in the planar view as much as the distance L3 set in such a manner. In other words, the end part 741 of the light blocking section 74 is disposed at the position away from the p-n junction part 735 toward the outside of the amplifier circuit 73 as much as the distance L3 described above in the planar view. In other words, the end part 741 of the light blocking section 74 is located between the p-n junction part 735 and the photodiode 72 in the cross-sectional view from the direction perpendicular to the normal direction of the surface 71A.

According to the above, even in the case in which the light with the assumed intensity described above has entered the light receiving element 7, it is prevented that the light from the end part of the light blocking section 74 indirectly reaches the p-n junction part 735 to exert a harmful influence on the amplifier circuit 73.

It should be noted that it is also possible to set the distance L3 described above to a larger distance than 300 μm regardless of the assumed intensity. However, in this case, there arises a possibility that the light blocking section 74 covers a part of the photodiode 72, and in addition, there arises a possibility that the distance between the photodiode 72 and the transistor TR1 increases to attenuate the signal input from the photodiode 72 to the transistor TR1. Therefore, it is preferable to make the distance L3 described above no more than 300 μm.

Distance Between p-n Junction Part of Photodiode and p-n Junction Part of Amplifier Circuit As described above, when the light enters the photodiode 72, the electric current flows in the anode electrode 723. However, there is a possibility that some of the electrons generated in a depletion layer in the vicinity of the p-n junction part 722 due to the incidence of the light migrate in the n-layer 711 of the silicon substrate 71, and then reach the p-n junction part (e.g., the p-n junction part 735 of the transistor TR1) of the amplifier circuit 73. If the electrons have reached the vicinity of the p-n junction part of the amplifier circuit 73, the amplifier circuit 73 malfunctions in some cases due to occurrence of the electric current caused by the electrons.

To cope with the above, in the present embodiment, the distance in the planar view between the p-n junction part 722 of the photodiode 72 and the p-n junction part provided to the amplifier circuit 73 is set to a distance of 100 μm or more and 300 μm or less. For example, assuming that the nearest p-n junction part to the p-n junction part 722 of the photodiode 72 in the amplifier circuit 73 is the p-n junction part 735 of the transistor TR1 as shown in FIG. 7, the distance L4 in the planar view between the p-n junction part 722 and the p-n junction part 735 is set to a distance in a range of 100 μm or more and 300 μm or less.

Thus, it is possible to prevent the electrons leaked from the photodiode 72 from reaching the p-n junction part of the amplifier circuit 73, and thus, it is possible to prevent the amplifier circuit 73 from malfunctioning.

It should be noted that it is also possible to set the distance L4 described above to a larger distance than 300 μm. However, in this case, similarly to the above, there arises a possibility that the distance between the photodiode 72 and the transistor TR1 becomes long, and thus the signal input from the photodiode 72 to the transistor TR1 is attenuated. Therefore, it is preferable to make the distance L4 described above no more than 300 μm.

Advantages of First Embodiment

The biological information measurement device 1 according to the present embodiment described hereinabove has the following advantages.

The light receiving element 7 has a configuration in which the photodiode 72, the amplifier circuit 73 for amplifying the output signal from the photodiode 72, and the light blocking section 74 for covering at least a part of the amplifier circuit 73 to block the light are disposed on the silicon substrate 71. According to this configuration, it is possible to prevent the light from entering the amplifier circuit 73 using the light blocking section 74. Therefore, it is possible to prevent the malfunction of the amplifier circuit 73 from occurring.

Further, since the light receiving module RMA equipped with the light receiving element 7, the processing circuit 62 for processing the output signal of the light receiving element 7, and the board 61 on which the light receiving element 7 and the processing circuit 62 are disposed can exert the advantages due to the light receiving element 7, and can additionally reduce the influence of signal attenuation in the circuit, it is possible to enhance the degree of freedom of the layout of the processing circuit 62 in the board 61. The same applies to the biological information detection sensor 6A as a photoelectric sensor equipped with the light emitting element 65 and the light receiving module described above.

Further, since the biological information measurement device 1 is equipped with the biological information detection sensor 6A and the circuit board 5 for determining the pulse rate as the biological information based on the pulse wave signal output from the biological information detection sensor 6A, it is possible to improve the measurement accuracy of the biological information.

The light blocking section 74 includes the aluminum layer. According to this configuration, it is possible to constitute the light blocking section 74 with a relatively simple configuration. Further, since the anode electrode 723 and the cathode electrode 724 of the photodiode 72, and the interconnection sections such as the conductive layers TR11, TR12 of the amplifier circuit 73 are formed on the silicon substrate 71 with the aluminum layer, it is possible to form the light blocking section 74 in substantially the same procedure. Similarly, since the protecting section 75 is the $SiO_2$ layer similarly to the insulating layers LY1, LY2 provided to the light receiving element 7, the protecting section 75 can also be formed in substantially the same procedure as that of the insulating layers LY1, LY2. Therefore, compared to the case of forming the light blocking section 74 with other materials, it is possible to easily and simply form the light blocking section 74.

Here, there is a possibility that a part of the light entering the light receiving element 7 circumvents the end part of the light blocking section 74 due to diffraction or the like, and then proceeds toward the amplifier circuit 73 at least partially covered with the light blocking section 74. Further, if the light enters the p-n junction part (e.g., the p-n junction part 735) provided to the amplifier circuit 73, there is a possibility that the electric current occurs due to the photovoltaic effect to cause the malfunction in the amplifier circuit 73.

To cope with the above, the amplifier circuit 73 has the p-n junction part 735 formed on the surface 71A as the first surface of the silicon substrate 71, and the end part of the light blocking section 74 is located between the p-n junction part 735 and the photodiode 72 in the cross-sectional view from the direction perpendicular to the normal direction of the surface 71A. According to this configuration, it is possible to reduce the possibility that the light circumventing the end part of the light blocking section 74 enters the p-n junction part 735, and it is possible to prevent an unintended electric current from occurring in the p-n junction part 735. Therefore, it is possible to prevent the malfunction of the amplifier circuit 73.

The end part 741 of the light blocking section 74 is disposed at the position away from the p-n junction part 735 toward the outside of the amplifier circuit 73 as much as the distance L3 100 µm or more and 300 µm or less in the planar view. According to this configuration, it is possible to prevent the light from circumventing the end part 741 of the light blocking section 74 to enter the p-n junction part 735 of the amplifier circuit 73. Therefore, it is possible to more effectively prevent the malfunction of the amplifier circuit 73.

Further, since the distance L3 does not exceed 300 µm, it is possible to dispose the amplifier circuit 73 in the vicinity of the photodiode 72. Thus, it is possible to prevent the output signal of the photodiode 72 to be input to the amplifier circuit 73 from attenuating, and it is possible to amplify the output signal of the photodiode 72 with the amplifier circuit 73.

The amplifier circuit 73 includes the charge-voltage conversion circuit CR1 for converting the charge output from the photodiode 72 into a voltage. The charge-voltage conversion circuit CR1 is provided with the transistor TR1 the gate of which is coupled to the anode of the photodiode 72, and the constant current source CS to be coupled to the drain of the transistor TR1. Further, the light blocking section 74 covers at least an area between the anode and the gate. According to this configuration, it is possible for the amplifier circuit 73 to amplify the output signal from the photodiode 72. Further, since the light blocking section 74 covers the area between the anode of the photodiode 72 and the gate of the transistor TR1, it is possible to prevent the light from entering the p-n junction part 735 of the transistor TR1. Therefore, it is possible to prevent the malfunction of the amplifier circuit 73 from occurring.

In the sensor section 64, the distance L1 between the light emitting element 65 and the photodiode 72 is shorter than the distance L2 between the light emitting element 65 and the input region C73 of the amplifier circuit 73. According to this configuration, it is possible to make it easy to make the light emitted from the light emitting element 65 to the living body as the detection target, and then reflected by the living body enter the photodiode 72. Thus, it is possible to improve the detection sensitivity of the light, and by extension, the detection sensitivity of the biological information, by the biological information detection sensor 6A as the photoelectric sensor. Further, since the amplifier circuit 73 is installed at the position farther from the light emitting element 65 than the photodiode 72, it is possible to reduce the influence of the light emitted from the light emitting element 65 on the amplifier circuit 73.

The amplifier circuit 73 is disposed in the direction from the photodiode 72, the direction being perpendicular to the direction from the photodiode 72 toward the light emitting element 65. According to this configuration, it is possible to make the distance L1 described above shorter than the distance L2 described above. Therefore, it is possible to improve the detection sensitivity of the light, and by extension, the detection sensitivity of the biological information, by the biological information detection sensor 6A, and in addition, it is possible to reduce the influence of the light emitted from the light emitting element 65 on the amplifier circuit 73.

The sensor section 64 has the shield section 66 which is disposed between the light emitting element 65 and the photodiode 72, and which blocks the light directly entering the photodiode 72 from the light emitting element 65. According to this configuration, it is possible to block the light directly entering the photodiode 72 from the light emitting element 65 using the shield section 66. Therefore, it is possible to improve the detection sensitivity of the light, and by extension, the detection sensitivity of the biological information, by the biological information detection sensor 6A.

First Modified Example of First Embodiment

In the biological information measurement device 1, it is assumed that the amplifier circuit 73 has the charge-voltage conversion circuit CR1, and the anode electrode 723 of the photodiode 72 is coupled to the gate of the transistor TR1. However, this is not a limitation, and providing the amplifier circuit can amplify the output signal from the photodiode, the configuration of the amplifier circuit is not limited to the above.

Figure 10:
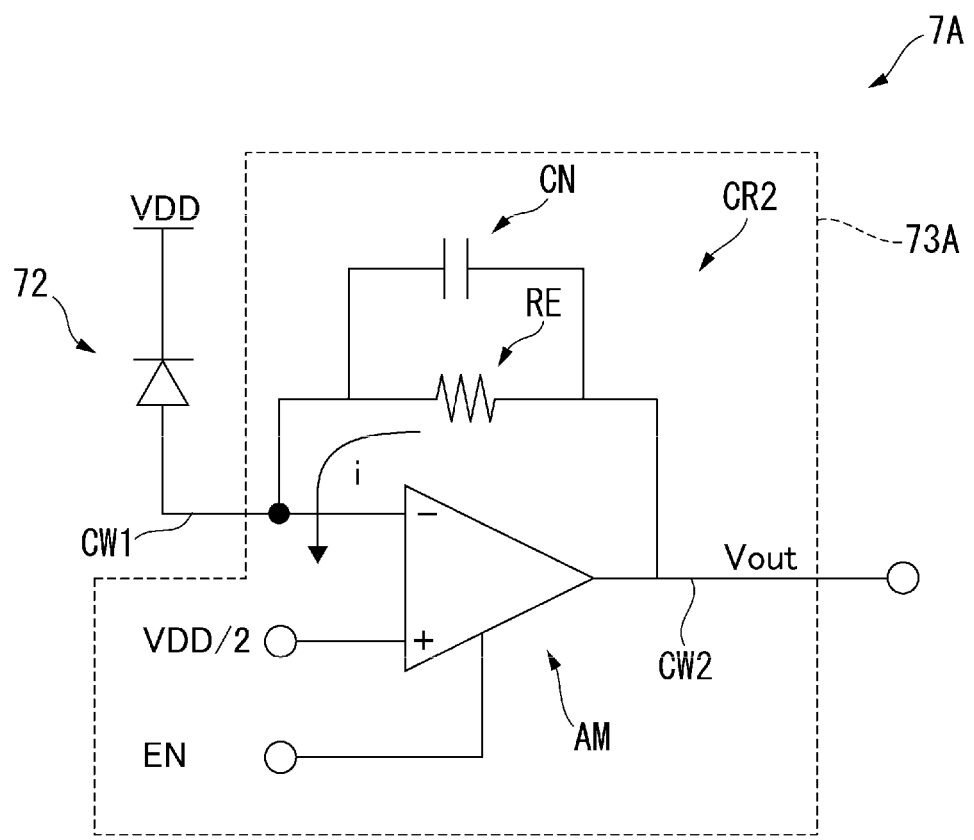
FIG. 10 is a circuit diagram showing a modification of the light receiving element in the first embodiment described above.

FIG. 10 is a circuit diagram showing a light receiving element 7A as a modification of the light receiving element 7.

For example, it is possible to adopt the light receiving element 7A shown in FIG. 10 in the sensor section 64, and by extension, in the biological information detection sensor 6A instead of the light receiving element 7.

The light receiving element 7A has substantially the same configuration as the light receiving element 7 except the point that an amplifier circuit 73A is provided instead of the amplifier circuit 73.

The amplifier circuit 73A amplifies the output signal from the photodiode 72 similarly to the amplifier circuit 73. The amplifier circuit 73A includes a current-voltage conversion circuit CR2 having an operational amplifier AM, a resistor RE and a capacitor CN.

The operational amplifier AM has an inverting input terminal to which the anode of the photodiode 72 is coupled, a non-inverting input terminal coupled to the ground, and an output terminal. The inverting input terminal of the operational amplifier AM is a region corresponding to the input region C73 described above.

The resistor RE is coupled in parallel to the operational amplifier AM. In the detailed description, the resistor RE is connected to an input line CW1 connecting the anode of the photodiode 72 and the inverting input terminal of the operational amplifier AM to each other, and an output line CW2 extending from the output terminal of the operational amplifier AM.

The capacitor CN is coupled in parallel to the operational amplifier AM similarly to the resistor RE. In the detailed description, the capacitor CN is connected to the input line CW1 and the output line CW2. The capacitor CN prevents the oscillation in the current-voltage conversion circuit CR2.

In such a current-voltage conversion circuit CR2, the gain of the output signal of the photodiode 72 is determined by the resistance value of the resistor RE, and the output signal thus amplified is output to the output line CW2.

Therefore, among the resistor RE and the capacitor CN, at least the resistor RE can externally be attached to the light receiving element 7A. Further, the resistor RE can also be a variable resistor. In this case, it is possible to provide the current-voltage conversion circuit CR2 with an automatic gain control (AGC) circuit for changing the resistance value of the resistor RE, namely the gain of the operational amplifier AM, in accordance with the signal level of the output signal input from the output line CW2.

Such an amplifier circuit 73A also makes it possible to amplify the output signal from the photodiode 72 similarly to the amplifier circuit 73 described above.

Further, also in the light receiving element 7A, the light blocking section 74 is disposed in, for example, the following manner.

In the case in which the assumed intensity described above is lower than 500 lux, the light blocking section 74 is disposed so as to cover the range from the output of the photodiode 72 (e.g., the end part on the amplifier circuit 73 side in the p-layer 721) to the inverting input terminal of the operational amplifier AM.

In the case in which the assumed intensity is lower than 5,000 lux, the light blocking section 74 is disposed so as to cover the range from the output of the photodiode 72 to the whole of the operational amplifier AM.

In the case in which the assumed intensity is lower than 10,000 lux, the light blocking section 74 is disposed so as to cover the range from the output of the photodiode 72 to the whole of the amplifier circuit 73A.

In the case in which the assumed intensity is no lower than 10,000 lux, the light blocking section 74 formed of a plurality of layers is disposed so as to cover the range from the output of the photodiode 72 to the whole of the amplifier circuit 73A.

As described above, since the light blocking section 74 covers the area between the anode of the photodiode 72 and the inverting input terminal of the operational amplifier AM, it is possible to reduce the influence of the light on the amplifier circuit 73A, and in addition, it is possible to reduce the influence of the light on the output signal of the photodiode 72 to be input to the inverting input terminal. Therefore, according also to the biological information measurement device 1 equipped with the light receiving element 7A, substantially the same advantages as in the biological information measurement device 1 equipped with the light receiving element 7 can be exerted.

Second Modified Example of First Embodiment

In the sensor section 64 of the biological information measurement device 1, it is assumed that the light emitting element 65 is located on the −Y direction side with respect to the photodiode 72, and the amplifier circuit 73 is located on the +X direction side with respect to the photodiode 72. However, the orientation of the amplifier circuit can be other orientations.

Figure 11:
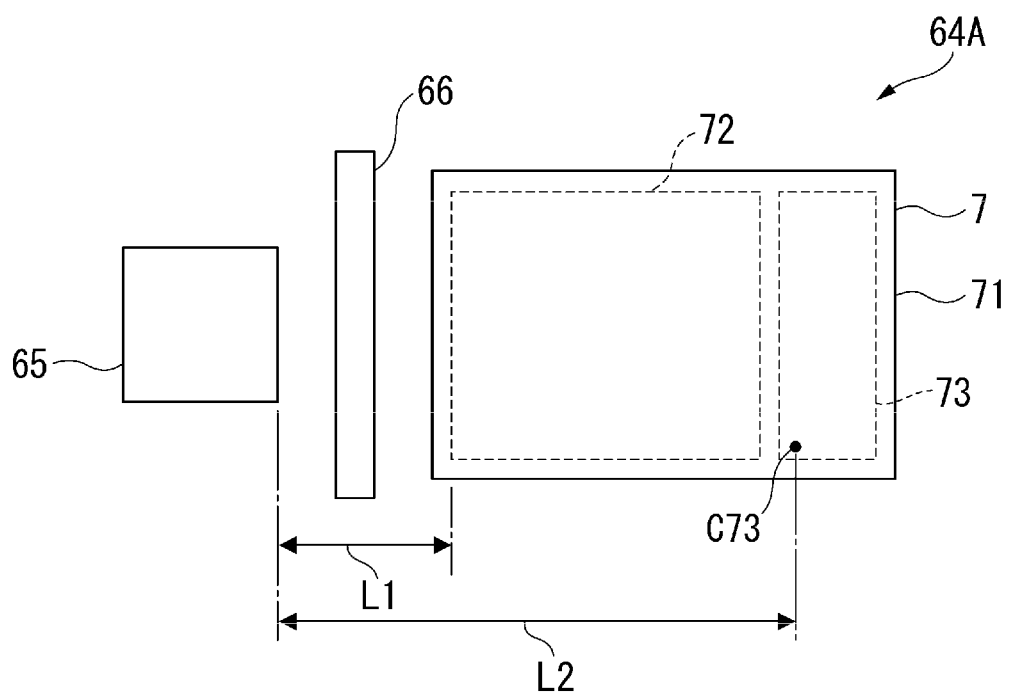
FIG. 11 is a schematic diagram showing a modification of a sensor section in the first embodiment described above.

FIG. 11 is a schematic diagram showing a part of a sensor section 64A as a modification of the sensor section 64.

For example, it is also possible to adopt the sensor section 64A shown in FIG. 11 in the biological information detection sensor 6A instead of the sensor section 64.

Similarly to the sensor section 64, the sensor section 64A has the light emitting element 65, the shield section 66 and the light receiving element 7, and the sealing section 67 which is formed of light transmissive sealing resin, and which seals the light emitting element 65, the shield section 66 and the light receiving element 7. It should be noted that the shield section 66 is disposed between the light emitting element 65 and the light receiving element 7.

In the sensor section 64A, the light receiving element 7 is arranged so that the amplifier circuit 73 is disposed at a position on the opposite side to the light emitting element 65 with respect to the photodiode 72 in the planar view. Therefore, also in the sensor section 64A, the distance L1 between the light emitting element 65 and the photodiode 72 is shorter than the distance L2 between the light emitting element 65 and the input region C73 of the amplifier circuit 73. It should be noted that the position of the input region C73 shown in FIG. 11 is also illustrative only.

By arranging the light receiving element 7 in such an orientation, since it is possible to make it easy to make the light emitted from the light emitting element 65, and then proceeding via the living body enter the photodiode 72 similarly to the layout of the sensor section 64 described above, it is possible to improve the detection sensitivity of the light by the biological information detection sensor 6A. Besides the above, since it is possible to prevent the light emitted from the light emitting element 65 from entering the amplifier circuit 73, it is possible to prevent the malfunction of the amplifier circuit 73 due to incidence of the light.

Second Embodiment

Then, a second embodiment of the present disclosure will be described.

The biological information measurement device according to the present embodiment is provided with substantially the same configuration as that of the biological information measurement device 1 shown in the first embodiment, but is different from the biological information measurement device 1 in the point that the light receiving element has a blocking section for blocking the electrons migrating from the photodiode toward the amplifier circuit. It should be noted that in the description below, a part which is the same or substantially the same as the part having already been described is denoted by the same reference symbol, and the description thereof will be omitted.

Figure 12:
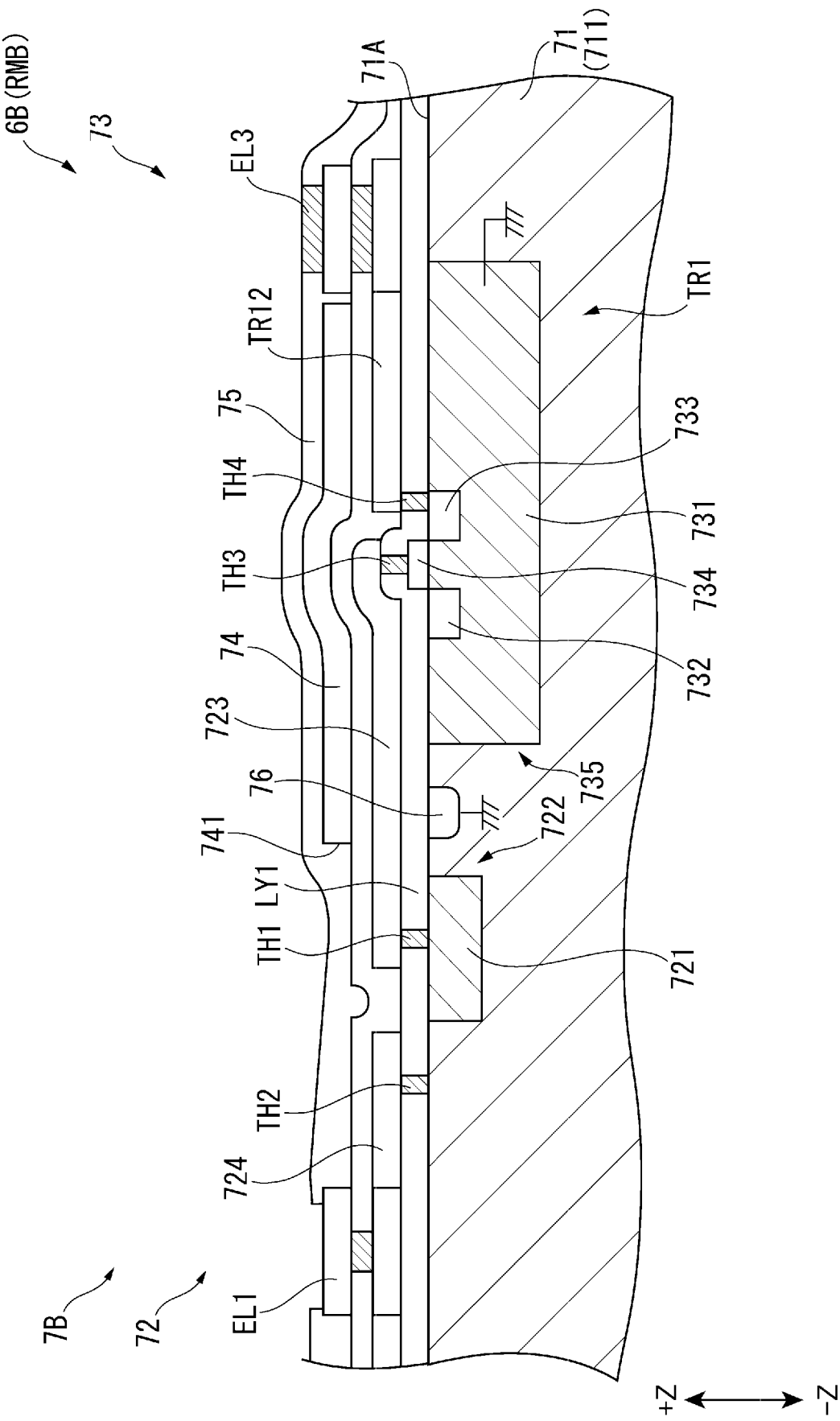
FIG. 12 is a schematic diagram showing a layer structure of a light receiving element provided to a biological information measurement device according to a second embodiment of the present disclosure.

FIG. 12 is a schematic diagram showing a layer structure of the light receiving element 7B provided to the biological information measurement device according to the present embodiment. It should be noted that in FIG. 12, some of the constituents of the light receiving element 7B are displayed in an enlarged manner to the extent that the constituents can visually be recognized.

The biological information measurement device according to the present embodiment has substantially the same configuration and functions as those of the biological information measurement device 1 except the point that the light receiving element 7B is provided instead of the light receiving element 7. In other words, the biological information measurement device according to the present embodiment is provided with the biological information detection sensor 6B having the light receiving element 7B as the photoelectric sensor. Further, the light receiving module RMB is constituted by the light receiving element 7B, the processing circuit 62 for processing the output signal of the light receiving element 7B, and the board 61 on which the light receiving element 7B and the processing circuit 62 are disposed.

As shown in FIG. 12, the light receiving element 7B has the silicon substrate 71, and the photodiode 72, the amplifier circuit 73, the light blocking section 74 and the protecting section 75 each disposed on the silicon substrate 71, and additionally has a blocking section 76. It should be noted that it is also possible for the light receiving element 7B to be provided with a configuration having the amplifier circuit 73A including the current-voltage conversion circuit CR2 instead of the amplifier circuit 73 including the charge-voltage conversion circuit CR1. Further, the orientation of the light receiving element 7B with respect to the light emitting element 65 can be the same as in the sensor section 64, and can also be the same as in the sensor section 64A.

The blocking section 76 is disposed between the photodiode 72 and the amplifier circuit 73. In the detailed description, the blocking section 76 is disposed between the p-n junction part 722 of the photodiode 72 and the p-n junction part nearest to the p-n junction part 722 in the amplifier circuit 73 in the silicon substrate 71, and blocks the electrons migrating from the p-n junction part 722 toward the p-n junction part of the amplifier circuit 73.

In the detailed description, the blocking section 76 is coupled to the ground of the amplifier circuit 73. Further, by making the electrons migrating in the n-layer 711 of the silicon substrate 71 from, for example, the p-n junction part 722 toward the p-n junction part of the amplifier circuit 73 flow to the ground of the amplifier circuit 73, the electrons are prevented from reaching the p-n junction part of the amplifier circuit 73. In other words, the blocking section 76 can also be said to be an electron capturing section.

In the present embodiment, in the amplifier circuit 73, the nearest p-n junction part to the p-n junction part 722 is the p-n junction part 735 of the transistor TR1. Therefore, the blocking section 76 is disposed between the p-n junction part 722 and the p-n junction part 735. Further, the blocking section 76 is disposed in a region to be covered with the light blocking section 74 in the planar view of the light receiving element 7B.

Such a blocking section 76 is a diode formed on the silicon substrate 71, and connected to the ground of the amplifier circuit 73.

Advantages of Second Embodiment

The biological information measurement device according to the present embodiment described hereinabove provides the same advantages as those of the biological information measurement device 1, and can further provide the following advantages.

If the electrons generated in the p-n junction part of the photodiode migrate in the silicon substrate, and then reach the p-n junction part of the amplifier circuit, an electric current is generated in the amplifier circuit, and the amplifier circuit malfunctions.

To cope with the above, the light receiving element 7B has the blocking section 76 which is disposed between the photodiode 72 and the amplifier circuit 73 in the silicon substrate 71, which is connected to the ground, and which blocks the electrons migrating in the silicon substrate 71 toward the amplifier circuit 73. According to this configuration, it is possible to prevent the electrons migrating from the photodiode 72 toward the amplifier circuit 73 from reaching the p-n junction part (e.g., the p-n junction part 735) of the amplifier circuit 73. Therefore, it is possible to effectively prevent the malfunction of the amplifier circuit 73.

The blocking section 76 is a diode to be connected to the ground of the amplifier circuit 73. According to this configuration, the blocking section 76 can easily be constituted, and in addition, it is possible to block the electrons migrating in the silicon substrate 71 toward the amplifier circuit 73. Therefore, it is possible to more effectively prevent the malfunction of the amplifier circuit 73.

Modifications of Embodiments

The present disclosure is not limited to each of the embodiments described above, but includes modifications, improvements, and so on within the range in which the advantages of the present disclosure can be achieved.

In each of the embodiments described above, it is assumed that the light blocking section 74 mainly covers the gate of the transistor TR1 or the inverting input terminal of the operational amplifier AM in the amplifier circuit 73. However, this is not a limitation, and the installation position of the light blocking section 74 is not limited to the above, and in addition, the configuration and the material of the light blocking section 74 can arbitrarily be changed. For example, as described above, the light blocking section 74 is not required to have the configuration of including the aluminum layer, but has a configuration including other metal layers or a resin layer. Besides the above, it is also possible for the light blocking section 74 to be provided with a configuration having a plurality of layers including the aluminum layer, and other metal layers or the resin layer.

Further, it is assumed that the silicon substrate 71 is an n-type silicon wafer, but the silicon substrate 71 can be a p-type silicon wafer.

In each of the embodiments described above, it is assumed that the distance L3 in the planar view between the end part 741 of the light blocking section 74 and the p-n junction part 735 of the amplifier circuit 73 is 100 µm or more and 300 µm or less. However, this is not a limitation, and the distance L3 can arbitrarily be changed. For example, when the photoelectric sensor is used in the environment in which the outside light hardly enters the photoelectric sensor, the distance L3 can also be set to a value shorter than 100 µm.

In other words, the distance L3 can be zero. Further, in the case in which the intensity of the light emitted from the light emitting element 65 is high, and the signal level of the output signal from the photodiode 72 is high, and so on, the distance L3 can also be a value exceeding 300 µm.

In the second embodiment described above, it is assumed that the blocking section 76 is formed of a diode. However, this is not a limitation, and providing the blocking section 76 is capable of blocking the electrons migrating in the silicon substrate 71 toward the amplifier circuit 73, 73A, the blocking section 76 is not limited to the diode, but can be other constituents such as a resistor.

Further, it is assumed that the ground to which the blocking section 76 is connected is the ground of the amplifier circuit 73. However, this is not a limitation, and it is also possible to separately provide the light receiving element with the ground to which the blocking section 76 is connected.

In each of the embodiments described above, it is assumed that the amplifier circuit 73 includes the charge-voltage conversion circuit CR1, and the amplifier circuit 73A includes the current-voltage conversion circuit CR2. However, this is not a limitation, and providing the amplifier circuit can amplify the output signal of the photodiode 72, the configuration of the amplifier circuit is not limited to the above.

In each of the embodiments described above, it is assumed that the biological information detection sensor 6A, 6B is provided with the board 61, the processing circuit 62, the connector 63 and the sensor section 64, 64A, and the sensor section 64, 64A has the light emitting element 65, the shield section 66, the sealing section 67 and the light receiving element 7, 7A, 7B. Among these constituents, the processing circuit 62 and the light receiving element 7, 7A, 7B can be disposed on the board 61 to thereby be configured as the light receiving module.

Further, it is also possible to configure a photoelectric sensor having the light emitting element 65 and any one of the light receiving elements 7, 7A, and 7B disposed on the board 61. In this case, it is also possible to dispose the processing circuit on a circuit board to electrically be coupled to the photoelectric sensor.

In each of the embodiments described above, it is assumed that the sensor section 64, 64A has the light emitting element 65 as the packaged LED chip. However, this is not a limitation, and it is also possible for the light emitting element 65 to be an unpackaged LED chip, namely a bare LED chip. Further, the light receiving element 7, 7A, 7B is assumed to be an unpackaged light receiving chip, but can also be a light receiving chip in which the region corresponding to the amplifier circuit 73, 73A is packaged. In this case, if the sealing region for sealing the amplifier circuit 73 is formed of a non-light transmissive material, it is possible to configure the sealing region as the light blocking section.

In each of the embodiments described above, it is assumed that the living body contact surface 671 is a convexly curved surface. However, this is not a limitation, and the shape of the surface on the light emission direction side in the sealing section 67 can also be another shape.

For example, the living body contact surface 671 can include a flat surface, or can also be a concavely curved surface. In the case in which the living body contact surface 671 is a concavely curved surface, it is possible to make it easy to diffuse the light emitted from the light emitting element 65 to the outside of the sealing section 67, and it is possible to make it easy to converge the light entering the sealing section 67 on the light receiving element 7, 7A, 7B.

By changing the shape and the curvature of the living body contact surface 671 as described above, it is possible to effectively irradiate the living body with the light emitted from the light emitting element 65 in accordance with the purpose of the biological information detection sensor, and in addition, it is possible to make the light entering the living body contact surface 671 efficiently enter the light receiving element 7, 7A, 7B.

In each of the embodiments described above, it is assumed that the processing circuit 62, the connector 63 and the sensor section 64, 64A are disposed on the mounting surface 61A on which the sensor section 64, 64A is located in the board 61. In other words, it is assumed that all of the constituents disposed on the board 61 are disposed on the mounting surface 61A. However, this is not a limitation, and among the plurality of constituents to be disposed on the board 61, at least one of the constituents except the sensor section 64 can be disposed on the reverse surface 61B on the opposite side to the mounting surface 61A. Since the recessed pars such as the recessed parts 223, 224 becomes unnecessary by adopting such a configuration, a thin wall part is eliminated in the back side part 22, and thus, it is possible to increase the strength of the housing 2.

In each of the embodiments described above, it is assumed that the sensor section 64, 64A has the single light emitting element 65 and the single light receiving element 7, 7A, 7B. However, this is not a limitation, and the number of the light emitting elements and the number of the light receiving elements can arbitrarily be changed. For example, it is possible to provide one light emitting element with respect to one light receiving element, or provide two or more light emitting elements with respect to one light receiving element. Further, it is also possible to provide two or more light receiving elements with respect to one light emitting element.

Further, it is also possible to provide a plurality of sets of elements, each including at least one light emitting element and at least one light receiving element. In this case, the sets of the light emitting element and the light receiving element can be sealed with a plurality of sealing sections set by set. Further, in this case, it is also possible to provide the back side part 22 with opening parts for exposing the respective sets of the light emitting element and the light receiving element.

Further, it is assumed that the distance L1 between the light emitting element 65 and the photodiode 72 is shorter than the distance L2 between the light emitting element 65 and the input region C73 of the amplifier circuit 73. However, this is not a limitation, and the layout of the light emitting element 65 and the light receiving element 7, 7A, 7B, and the orientation of the light receiving element 7, 7A, 7B can arbitrarily be changed. For example, it is also possible to arrange the light emitting element and the light receiving element side by side in the +X direction.

Further, it is assumed that in the sensor section 64, the amplifier circuit 73 is disposed in the direction from the photodiode 72, the direction being perpendicular to the direction from the photodiode 72 toward the light emitting element 65. Further, it is assumed that in the sensor section 64A, the amplifier circuit 73 is disposed at the position on the opposite side to the light emitting element 65 with respect to the photodiode 72. However, the position of the amplifier circuit 73 can arbitrarily be changed. Specifically, providing the amplifier circuit 73 is disposed at a position farther to the light emitting element 65 than the photodiode 72, the advantages described above can be obtained. For example, it is also possible for the amplifier circuit 73 to be located in the direction from the photodiode 72, the direction crossing the direction from the photodiode 72 toward the light emitting element 65 at a predetermined angle. In this case, it is also possible for the amplifier circuit 73 to be located in the direction from the photodiode 72, the direction crossing the direction from the photodiode 72 toward the light emitting element 65 at an obtuse angle.

In each of the embodiments described above, it is assumed that the sensor section 64, 64A has the shield section 66. However, this is not a limitation, and the shield section 66 can be eliminated. Further, even in the case in which the shield section 66 is disposed, the shape of the shield section 66 can arbitrarily be changed as described above.

Further, the position of the tip part 661 on the +Z direction side in the shield section 66 can also be changed as described above. Specifically, the position of the tip part 661 can be on the −Z direction side or the +Z direction side with respect to the living body contact surface 671, or can coincide with the living body contact surface 671.

In each of the embodiments described above, it is assumed that the sensor section 64, 64A is provided to the biological information detection sensor 6A, 6B. However, this is not a limitation, and it is also possible for the sensor section 64, 64A to be disposed on the circuit board 5. Specifically, it is also possible to dispose the constituents of the circuit board 5 and the constituents of the biological information detection sensor 6A, 6B on one board so as to have the function of the circuit board 5 and the function of the biological information detection sensor 6A, 6B. Further, the position of the battery 3 can arbitrarily be changed.

In each of the embodiments described above, it is assumed that the light emitting element 65, the shield section 66 and the light receiving element 7, 7A, 7B are sealed on the mounting surface 61A of the board 61 by the sealing section 67. However, this is not a limitation, and such a sealing section can be eliminated. In this case, it is also possible to provide, for example, a light transmissive member which closes the opening part 221 having the light emitting element 65, the shield section 66 and the light receiving element 7, 7A, 7B disposed inside in the planar view, and which can transmit the light emitted from the light emitting element 65 and the light to be received by the light receiving element 7, 7A, 7B.

In each of the embodiments described above, it is assumed that the circuit board 5 is provided with the acceleration sensor for detecting the acceleration acting on the measurement device. However, this is not a limitation, and it is not required to provide the circuit board 5 with the acceleration sensor, and further, even in the case in which the acceleration sensor is provided, the acceleration sensor can be provided to other constituents than the circuit board 5. For example, other sensors such as the acceleration sensor can be disposed on the board 61 of the biological information detection sensor 6A, 6B. Further, it is also possible for the biological information measurement device to be equipped with a position sensor (e.g., a GPS receiver) capable of measuring the positional information.

In each of the embodiments described above, it is assumed that the biological information detection sensor 6A, 6B detects the pulse wave as a type of the biological information, and then the circuit board 5 determines the pulse rate as another type of the biological information based on the pulse wave signal output from the biological information detection sensor 6A, 6B. In other words, it is assumed that the biological information measurement device 1 described above measures the pulse wave and the pulse rate as the biological information. However, this is not a limitation, and the biological information which can be detected and measured by the biological information measurement device according to the present disclosure is not limited to the pulse wave and the pulse rate. It is also possible to apply the present disclosure to a biological information measurement device for measuring biological information such as heart rate variability (HRV), a pulse interval (R-R interval (RRI)), blood pressure, a blood sugar level, an amount of activity, calorie consumption, or maximum oxygen uptake ($VO_2$max) using a photoelectric sensor including a light receiving module.

In each of the embodiments described above, it is assumed that the biological information detection sensor 6A, 6B is a sensor for detecting the biological information, and has the light receiving module RMA, RMB including the light receiving element 7. However, the purposes of the light receiving element, the light receiving module and the photoelectric sensor according to the present disclosure are not limited to the detection of the biological information. For example, it is also possible to adopt the light receiving element, the light receiving module and the photoelectric sensor according to the present disclosure in the purpose of position detection of a vehicle and so on.

What is claimed is:
1. A light receiving element comprising:
  a silicon substrate;
  a photodiode adapted to detect light;
  an amplifier circuit adapted to amplify an output signal from the photodiode; and
  a light blocking section adapted to cover at least a part of the amplifier circuit to block the light, wherein
  the photodiode, the amplifier circuit and the light blocking section are provided to the silicon substrate, the silicon substrate has a first surface on which the photodiode and the amplifier circuit are disposed, the amplifier circuit has a p-n junction part on the first surface, and an end part of the light blocking section is located between the p-n junction part and the photodiode in a cross-sectional view from a direction perpendicular to a normal line of the first surface.

2. The light receiving element according to claim 1, wherein
the light blocking section includes an aluminum layer.

3. The light receiving element according to claim 2, wherein
the silicon substrate has a first surface on which the photodiode and the amplifier circuit are disposed, the amplifier circuit has a p-n junction part on the first surface, and an end part of the light blocking section is located between the p-n junction part and the photodiode in a cross-sectional view from a direction perpendicular to a normal line of the first surface.

4. The light receiving element according to claim 1, wherein
a distance from the end part of the light blocking section to the p-n junction part is 100 μm or more and no more than 300 μm viewed from a normal direction of the first surface.

5. The light receiving element according to claim 3, wherein
a distance from the end part of the light blocking section to the p-n junction part is 100 μm or more and no more than 300 μm viewed from a normal direction of the first surface.

6. The light receiving element according to claim 1, further comprising:
a blocking section disposed between the photodiode and the amplifier circuit in the silicon substrate, and adapted to block an electron migrating in the silicon substrate toward the amplifier circuit.

7. The light receiving element according to claim 2, further comprising:
a blocking section disposed between the photodiode and the amplifier circuit in the silicon substrate, and adapted to block an electron migrating in the silicon substrate toward the amplifier circuit.

8. The light receiving element according to claim 1, further comprising:
a blocking section disposed between the photodiode and the amplifier circuit in the silicon substrate, and adapted to block an electron migrating in the silicon substrate toward the amplifier circuit.

9. The light receiving element according to claim 3, further comprising:
a blocking section disposed between the photodiode and the amplifier circuit in the silicon substrate, and adapted to block an electron migrating in the silicon substrate toward the amplifier circuit.

10. The light receiving element according to claim 4, further comprising:
a blocking section disposed between the photodiode and the amplifier circuit in the silicon substrate, and adapted to block an electron migrating in the silicon substrate toward the amplifier circuit.

11. The light receiving element according to claim 5, further comprising:
a blocking section disposed between the photodiode and the amplifier circuit in the silicon substrate, and adapted to block an electron migrating in the silicon substrate toward the amplifier circuit.

12. The light receiving element according to claim 6, wherein
the blocking section is a diode to be connected to ground of the amplifier circuit.

13. The light receiving element according to claim 7, wherein
the blocking section is a diode to be connected to ground of the amplifier circuit.

14. The light receiving element according to claim 8, wherein
the blocking section is a diode to be connected to ground of the amplifier circuit.

15. The light receiving element according to claim 10, wherein
the blocking section is a diode to be connected to ground of the amplifier circuit.

16. The light receiving element according to claim 1, wherein
the amplifier circuit includes a charge-voltage conversion circuit adapted to convert a charge output from the photodiode into a voltage, the charge-voltage conversion circuit includes
a transistor a gate of which is connected to an anode of the photodiode and
a constant current source to be connected to a drain of the transistor, and the light blocking section covers at least an area between the anode and the gate.

17. The light receiving element according to claim 2, wherein
the amplifier circuit includes a charge-voltage conversion circuit adapted to convert a charge output from the photodiode into a voltage, the charge-voltage conversion circuit includes
a transistor a gate of which is connected to an anode of the photodiode and
a constant current source to be connected to a drain of the transistor, and the light blocking section covers at least an area between the anode and the gate.

18. The light receiving element according to claim 1, wherein
the amplifier circuit includes a current-voltage conversion circuit adapted to convert an electric current output from the photodiode into a voltage, the current-voltage conversion circuit includes
an operational amplifier having an inverting input terminal to which an anode of the photodiode is connected, a non-inverting input terminal to be connected to ground, and an output terminal from which the output signal converted is output and
a resistor and a capacitor each disposed in parallel to the operational amplifier, and the light blocking section covers at least an area between the anode and the inverting input terminal.

19. The light receiving element according to claim 2, wherein
the amplifier circuit includes a current-voltage conversion circuit adapted to convert an electric current output from the photodiode into a voltage, the current-voltage conversion circuit includes
an operational amplifier having an inverting input terminal to which an anode of the photodiode is connected, a non-inverting input terminal to be connected to ground, and an output terminal from which the output signal converted is output and a resistor and a capacitor each disposed in parallel to the operational amplifier, and the light blocking section covers at least an area between the anode and the inverting input terminal.

20. A light receiving module comprising:

the light receiving element according to claim 1;

a processing circuit adapted to process a signal output from the light receiving element; and a board on which the light receiving element and the processing circuit are disposed.

21. A photoelectric sensor comprising:

the light receiving module according to claim 20; and a light emitting element to be disposed on the board.

22. The photoelectric sensor according to claim 21, wherein a distance between the light emitting element and the photodiode is shorter than a distance between the light emitting element and an input region of an output signal from the photodiode in the amplifier circuit.

23. The photoelectric sensor according to claim 22, wherein the amplifier circuit is disposed in a direction from the photodiode, the direction being perpendicular to a direction from the photodiode toward the light emitting element.

24. The photoelectric sensor according to claim 22, wherein the amplifier circuit is disposed at a position on an opposite side to the light emitting element with respect to the photodiode.

25. The photoelectric sensor according to claim 21, further comprising:

a shield section disposed between the light emitting element and the photodiode, and adapted to block light directly entering the photodiode from the light emitting element.

* * * * *